(12) United States Patent
Defreitas et al.

(10) Patent No.: US 12,193,853 B2
(45) Date of Patent: Jan. 14, 2025

(54) BREAST BIOPSY AND NEEDLE LOCALIZATION USING TOMOSYNTHESIS SYSTEMS

(71) Applicant: Hologic, Inc., Marlborough, MA (US)

(72) Inventors: Kenneth Defreitas, Patterson, NY (US); John Laviola, Madison, CT (US); Loren Niklason, Tetonia, ID (US); Tao Wu, Brookfield, CT (US); Joseph Mark, Indianapolis, IN (US); Michael Miller, Trafalgar, IN (US); Jay Stein, Boston, MA (US); Andrew P. Smith, Lexington, MA (US)

(73) Assignee: Hologic, Inc., Marlborough, MA (US)

( * ) Notice: Subject to any disclaimer, the term of this patent is extended or adjusted under 35 U.S.C. 154(b) by 0 days.

(21) Appl. No.: 18/417,682

(22) Filed: Jan. 19, 2024

(65) Prior Publication Data

US 2024/0341698 A1 Oct. 17, 2024

Related U.S. Application Data

(63) Continuation of application No. 16/936,550, filed on Jul. 23, 2020, now Pat. No. 11,918,389, which is a
(Continued)

(51) Int. Cl.
*A61B 6/02* (2006.01)
*A61B 6/00* (2006.01)
*A61B 6/04* (2006.01)
*A61B 6/12* (2006.01)
*A61B 6/46* (2024.01)
(Continued)

(52) U.S. Cl.
CPC ............ *A61B 6/025* (2013.01); *A61B 6/0435* (2013.01); *A61B 6/463* (2013.01); *A61B 6/466* (2013.01); *A61B 6/467* (2013.01); *A61B 6/469* (2013.01); *A61B 6/502* (2013.01); *A61B 6/542* (2013.01); *A61B 10/0041* (2013.01); *A61B 10/0233* (2013.01); *A61B 10/0275* (2013.01); *A61B 90/11* (2016.02); *A61B 90/17* (2016.02);
(Continued)

(58) Field of Classification Search
CPC ................................ A61B 6/025; A61B 6/542
See application file for complete search history.

(56) References Cited

U.S. PATENT DOCUMENTS

| 3,502,878 A | 3/1970 | Stewart |
| 3,863,073 A | 1/1975 | Wagner |

(Continued)

FOREIGN PATENT DOCUMENTS

| AU | 2014339982 | 4/2015 |
| CN | 1802121 A | 7/2006 |

(Continued)

OTHER PUBLICATIONS

"Filtered Back Projection", (NYGREN), published May 8, 2007, URL: http://web.archive.org/web/19991010131715/http://www.owlnet.rice.edu/~elec539/Projects97/cult/node2.html, 2 pgs.
(Continued)

*Primary Examiner* — Colin T. Sakamoto
(74) *Attorney, Agent, or Firm* — Merchant & Gould P.C.

(57) ABSTRACT

Methods, devices, apparatuses and systems are disclosed for performing mammography, such as utilizing tomosynthesis in combination with breast biopsy.

20 Claims, 17 Drawing Sheets

System showing asymmetric tomo scan to avoid shadowing the gun stage

Related U.S. Application Data continuation of application No. 16/434,064, filed on Jun. 6, 2019, now Pat. No. 11,452,486, which is a continuation of application No. 15/904,735, filed on Feb. 26, 2018, now Pat. No. 10,335,094, which is a continuation of application No. 14/021,624, filed on Sep. 9, 2013, now Pat. No. 9,901,309, which is a continuation of application No. 11/707,587, filed on Feb. 15, 2007, now Pat. No. 8,532,745.

(60) Provisional application No. 60/774,142, filed on Feb. 15, 2006.

(51) Int. Cl.
| | | |
|---|---|---|
| *A61B 6/50* | (2024.01) | |
| *A61B 10/00* | (2006.01) | |
| *A61B 10/02* | (2006.01) | |
| *A61B 90/11* | (2016.01) | |
| *A61B 90/17* | (2016.01) | |
| *A61B 90/00* | (2016.01) | |

(52) U.S. Cl.
CPC .............. *A61B 6/0414* (2013.01); *A61B 6/12* (2013.01); *A61B 6/481* (2013.01); *A61B 2090/376* (2016.02)

(56) References Cited

U.S. PATENT DOCUMENTS

| | | |
|---|---|---|
| 3,971,950 A | 7/1976 | Evans et al. |
| 4,160,906 A | 7/1979 | Daniels |
| 4,310,766 A | 1/1982 | Finkenzeller et al. |
| 4,496,557 A | 1/1985 | Malen et al. |
| 4,559,557 A | 12/1985 | Keyes |
| 4,559,641 A | 12/1985 | Caugant et al. |
| 4,706,269 A | 11/1987 | Reina et al. |
| 4,727,565 A | 2/1988 | Ericson |
| 4,744,099 A | 5/1988 | Huettenrauch |
| 4,773,086 A | 9/1988 | Fujita |
| 4,773,087 A | 9/1988 | Plewes |
| 4,819,258 A | 4/1989 | Kleinman et al. |
| 4,821,727 A | 4/1989 | Levene et al. |
| 4,907,156 A | 6/1990 | Doi et al. |
| 4,969,174 A | 11/1990 | Schied |
| 4,989,227 A | 1/1991 | Tirelli et al. |
| 5,018,176 A | 5/1991 | Romeas et al. |
| RE33,634 E | 7/1991 | Yanaki |
| 5,029,193 A | 7/1991 | Saffer |
| 5,051,904 A | 9/1991 | Griffith |
| 5,078,142 A | 1/1992 | Siczek et al. |
| 5,099,846 A | 3/1992 | Hardy |
| 5,129,911 A | 7/1992 | Siczek et al. |
| 5,133,020 A | 7/1992 | Giger et al. |
| 5,163,075 A | 11/1992 | Lubinsky |
| 5,164,976 A | 11/1992 | Scheid et al. |
| 5,199,056 A | 3/1993 | Darrah |
| 5,219,351 A | 6/1993 | Teubner |
| 5,240,011 A | 8/1993 | Assa |
| 5,279,309 A | 1/1994 | Taylor et al. |
| 5,280,427 A | 1/1994 | Magnusson |
| 5,289,520 A | 2/1994 | Pellegrino et al. |
| 5,343,390 A | 8/1994 | Doi et al. |
| 5,359,637 A | 10/1994 | Webbe |
| 5,365,562 A | 11/1994 | Toker |
| 5,386,447 A | 1/1995 | Siczek |
| 5,415,169 A | 5/1995 | Siczek et al. |
| 5,426,685 A | 6/1995 | Pellegrino et al. |
| 5,452,367 A | 9/1995 | Bick |
| 5,491,627 A | 2/1996 | Zhang et al. |
| 5,499,097 A | 3/1996 | Ortyn et al. |
| 5,506,877 A | 4/1996 | Niklason et al. |
| 5,526,394 A | 6/1996 | Siczek |
| 5,539,797 A | 7/1996 | Heidsieck et al. |
| 5,553,111 A | 9/1996 | Moore |
| 5,592,562 A | 1/1997 | Rooks |
| 5,594,769 A | 1/1997 | Pellegrino et al. |
| 5,596,200 A | 1/1997 | Sharma |
| 5,598,454 A | 1/1997 | Franetzki |
| 5,609,152 A | 3/1997 | Pellegrino et al. |
| 5,627,869 A | 5/1997 | Andrew et al. |
| 5,642,433 A | 6/1997 | Lee et al. |
| 5,642,441 A | 6/1997 | Riley et al. |
| 5,647,025 A | 7/1997 | Frost et al. |
| 5,657,362 A | 8/1997 | Giger et al. |
| 5,660,185 A | 8/1997 | Shmulewitz et al. |
| 5,668,889 A | 9/1997 | Hara |
| 5,671,288 A | 9/1997 | Wilhelm et al. |
| 5,709,206 A | 1/1998 | Teboul |
| 5,712,890 A | 1/1998 | Spivey |
| 5,719,952 A | 2/1998 | Rooks |
| 5,735,264 A | 4/1998 | Siczek et al. |
| 5,757,880 A | 5/1998 | Colomb |
| 5,763,871 A | 6/1998 | Ortyn et al. |
| 5,769,086 A | 6/1998 | Ritchart et al. |
| 5,773,832 A | 6/1998 | Sayed et al. |
| 5,803,912 A | 9/1998 | Siczek et al. |
| 5,818,898 A | 10/1998 | Tsukamoto et al. |
| 5,828,722 A | 10/1998 | Ploetz |
| 5,835,079 A | 11/1998 | Shieh |
| 5,841,124 A | 11/1998 | Ortyn et al. |
| 5,872,828 A | 2/1999 | Niklason et al. |
| 5,875,258 A | 2/1999 | Ortyn et al. |
| 5,878,104 A | 3/1999 | Ploetz |
| 5,878,746 A | 3/1999 | Lemelson et al. |
| 5,896,437 A | 4/1999 | Ploetz |
| 5,941,832 A | 8/1999 | Tumey |
| 5,954,650 A | 9/1999 | Saito |
| 5,986,662 A | 11/1999 | Argiro |
| 6,005,907 A | 12/1999 | Ploetz |
| 6,022,325 A | 2/2000 | Siczek et al. |
| 6,067,079 A | 5/2000 | Shieh |
| 6,075,879 A | 6/2000 | Roehrig et al. |
| 6,091,841 A | 7/2000 | Rogers |
| 6,091,981 A | 7/2000 | Cundari et al. |
| 6,101,236 A | 8/2000 | Wang et al. |
| 6,102,866 A | 8/2000 | Nields et al. |
| 6,137,527 A | 10/2000 | Abdel-Malek |
| 6,141,398 A | 10/2000 | He |
| 6,149,301 A | 11/2000 | Kautzer et al. |
| 6,175,117 B1 | 1/2001 | Komardin |
| 6,196,715 B1 | 3/2001 | Nambu |
| 6,215,892 B1 | 4/2001 | Douglass et al. |
| 6,216,540 B1 | 4/2001 | Nelson |
| 6,219,059 B1 | 4/2001 | Argiro |
| 6,256,370 B1 | 4/2001 | Yavus |
| 6,233,473 B1 | 5/2001 | Sheperd |
| 6,243,441 B1 | 6/2001 | Zur |
| 6,245,028 B1 | 6/2001 | Furst et al. |
| 6,272,207 B1 | 8/2001 | Tang |
| 6,289,235 B1 | 9/2001 | Webber et al. |
| 6,292,530 B1 | 9/2001 | Yavus |
| 6,293,282 B1 | 9/2001 | Lemelson |
| 6,327,336 B1 | 12/2001 | Gingold et al. |
| 6,327,377 B1 | 12/2001 | Rutenberg et al. |
| 6,341,156 B1 | 1/2002 | Baetz |
| 6,375,352 B1 | 4/2002 | Hewes |
| 6,389,104 B1 | 5/2002 | Bani-Hashemi et al. |
| 6,411,836 B1 | 6/2002 | Patel |
| 6,415,015 B2 | 7/2002 | Nicolas |
| 6,424,332 B1 | 7/2002 | Powell |
| 6,442,288 B1 | 8/2002 | Haerer |
| 6,459,925 B1 | 10/2002 | Nields et al. |
| 6,463,181 B2 | 10/2002 | Duarte |
| 6,468,226 B1 | 10/2002 | McIntyre, IV |
| 6,480,565 B1 | 11/2002 | Ning |
| 6,501,819 B2 | 12/2002 | Unger et al. |
| 6,556,655 B1 | 4/2003 | Chichereau |
| 6,574,304 B1 | 6/2003 | Hsieh |
| 6,597,762 B1 | 7/2003 | Ferrant |
| 6,611,575 B1 | 8/2003 | Alyassin et al. |
| 6,620,111 B2 | 9/2003 | Stephens et al. |
| 6,626,849 B2 | 9/2003 | Huitema et al. |
| 6,633,674 B1 | 10/2003 | Barnes |

(56) References Cited

U.S. PATENT DOCUMENTS

| | | |
|---|---|---|
| 6,638,235 B2 | 10/2003 | Miller et al. |
| 6,647,092 B2 | 11/2003 | Eberhard |
| 6,650,928 B1 | 11/2003 | Gailly |
| 6,683,934 B1 | 1/2004 | Zhao |
| 6,744,848 B2 | 6/2004 | Stanton |
| 6,748,044 B2 | 6/2004 | Sabol et al. |
| 6,751,285 B2 | 6/2004 | Eberhard |
| 6,758,824 B1 | 7/2004 | Miller et al. |
| 6,813,334 B2 | 11/2004 | Koppe |
| 6,882,700 B2 | 4/2005 | Wang |
| 6,885,724 B2 | 4/2005 | Li |
| 6,901,156 B2 | 5/2005 | Giger et al. |
| 6,912,319 B1 | 5/2005 | Barnes |
| 6,940,943 B2 | 9/2005 | Claus |
| 6,978,040 B2 | 12/2005 | Berestov |
| 6,987,331 B2 | 1/2006 | Koeppe |
| 6,999,553 B2 | 2/2006 | Livingston |
| 6,999,554 B2 | 2/2006 | Mertelmeier |
| 7,022,075 B2 | 4/2006 | Grunwald et al. |
| 7,025,725 B2 | 4/2006 | Dione et al. |
| 7,030,861 B1 | 4/2006 | Westerman |
| 7,110,490 B2 | 9/2006 | Eberhard |
| 7,110,502 B2 | 9/2006 | Tsuji |
| 7,117,098 B1 | 10/2006 | Dunlay et al. |
| 7,123,684 B2 | 10/2006 | Jing et al. |
| 7,127,091 B2 | 10/2006 | OpDeBeek |
| 7,142,633 B2 | 11/2006 | Eberhard |
| 7,218,766 B2 | 5/2007 | Eberhard |
| 7,245,694 B2 | 7/2007 | Jing et al. |
| 7,286,634 B2 | 10/2007 | Sommer, Jr. et al. |
| 7,289,825 B2 | 10/2007 | Fors et al. |
| 7,298,881 B2 | 11/2007 | Giger et al. |
| 7,315,607 B2 | 1/2008 | Ramsauer |
| 7,319,735 B2 | 1/2008 | Defreitas et al. |
| 7,323,692 B2 | 1/2008 | Rowlands |
| 7,346,381 B2 | 3/2008 | Okerlund et al. |
| 7,406,150 B2 | 7/2008 | Minyard et al. |
| 7,430,272 B2 | 9/2008 | Jing et al. |
| 7,443,949 B2 | 10/2008 | Defreitas et al. |
| 7,466,795 B2 | 12/2008 | Eberhard et al. |
| 7,556,602 B2 | 7/2009 | Wang et al. |
| 7,577,282 B2 | 8/2009 | Gkanatsios et al. |
| 7,606,801 B2 | 10/2009 | Faitelson et al. |
| 7,616,801 B2 | 11/2009 | Gkanatsios et al. |
| 7,630,533 B2 | 12/2009 | Ruth et al. |
| 7,634,050 B2 | 12/2009 | Muller et al. |
| 7,640,051 B2 | 12/2009 | Krishnan |
| 7,697,660 B2 | 4/2010 | Ning |
| 7,702,142 B2 | 4/2010 | Ren et al. |
| 7,705,830 B2 | 4/2010 | Westerman et al. |
| 7,760,924 B2 | 7/2010 | Ruth et al. |
| 7,769,219 B2 | 8/2010 | Zahniser |
| 7,787,936 B2 | 8/2010 | Kressy |
| 7,809,175 B2 | 10/2010 | Roehrig et al. |
| 7,828,733 B2 | 11/2010 | Zhang et al. |
| 7,831,296 B2 | 11/2010 | DeFreitas et al. |
| 7,869,563 B2 | 1/2011 | DeFreitas |
| 7,974,924 B2 | 7/2011 | Holla et al. |
| 7,991,106 B2 | 8/2011 | Ren et al. |
| 8,044,972 B2 | 10/2011 | Hall et al. |
| 8,051,386 B2 | 11/2011 | Rosander et al. |
| 8,126,226 B2 | 2/2012 | Bernard et al. |
| 8,155,421 B2 | 4/2012 | Ren et al. |
| 8,165,365 B2 | 4/2012 | Bernard et al. |
| 8,532,745 B2 | 9/2013 | DeFreitas et al. |
| 8,571,289 B2 | 10/2013 | Ruth |
| 8,594,274 B2 | 11/2013 | Hoernig et al. |
| 8,677,282 B2 | 3/2014 | Cragun et al. |
| 8,712,127 B2 | 4/2014 | Ren et al. |
| 8,787,522 B2 | 7/2014 | Smith et al. |
| 8,897,535 B2 | 11/2014 | Ruth et al. |
| 8,983,156 B2 | 3/2015 | Periaswamy et al. |
| 9,020,579 B2 | 4/2015 | Smith |
| 9,075,903 B2 | 7/2015 | Marshall |
| 9,084,579 B2 | 7/2015 | Ren et al. |
| 9,119,599 B2 | 9/2015 | Itai |
| 9,129,362 B2 | 9/2015 | Jerebko |
| 9,289,183 B2 | 3/2016 | Karssemeijer |
| 9,451,924 B2 | 9/2016 | Bernard |
| 9,456,797 B2 | 10/2016 | Ruth et al. |
| 9,478,028 B2 | 10/2016 | Parthasarathy |
| 9,589,374 B1 | 3/2017 | Gao |
| 9,592,019 B2 | 3/2017 | Sugiyama |
| 9,805,507 B2 | 10/2017 | Chen |
| 9,808,215 B2 | 11/2017 | Ruth et al. |
| 9,811,758 B2 | 11/2017 | Ren et al. |
| 9,901,309 B2 | 2/2018 | DeFreitas et al. |
| 10,008,184 B2 | 6/2018 | Kreeger et al. |
| 10,010,302 B2 | 7/2018 | Ruth et al. |
| 10,074,199 B2 | 9/2018 | Robinson et al. |
| 10,092,358 B2 | 10/2018 | DeFreitas |
| 10,111,631 B2 | 10/2018 | Gkanatsios |
| 10,242,490 B2 | 3/2019 | Karssemeijer |
| 10,276,265 B2 | 4/2019 | Reicher et al. |
| 10,282,840 B2 | 5/2019 | Moehrle et al. |
| 10,335,094 B2 | 7/2019 | DeFreitas |
| 10,357,211 B2 | 7/2019 | Smith |
| 10,410,417 B2 | 9/2019 | Chen et al. |
| 10,413,263 B2 | 9/2019 | Ruth et al. |
| 10,444,960 B2 | 10/2019 | Marshall |
| 10,456,213 B2 | 10/2019 | DeFreitas |
| 10,573,276 B2 | 2/2020 | Kreeger et al. |
| 10,575,807 B2 | 3/2020 | Gkanatsios |
| 10,595,954 B2 | 3/2020 | DeFreitas |
| 10,624,598 B2 | 4/2020 | Chen |
| 10,977,863 B2 | 4/2021 | Chen |
| 10,978,026 B2 | 4/2021 | Kreeger |
| 11,701,199 B2 | 7/2023 | DeFreitas |
| 11,918,389 B2 | 3/2024 | DeFreitas |
| 2001/0038681 A1 | 11/2001 | Stanton et al. |
| 2001/0038861 A1 | 11/2001 | Hsu et al. |
| 2002/0012450 A1 | 1/2002 | Tsuji |
| 2002/0050986 A1 | 5/2002 | Inoue |
| 2002/0075997 A1 | 6/2002 | Unger et al. |
| 2002/0113681 A1 | 8/2002 | Byram |
| 2002/0122533 A1 | 9/2002 | Marie et al. |
| 2002/0188466 A1 | 12/2002 | Barrette et al. |
| 2002/0193676 A1 | 12/2002 | Bodicker |
| 2003/0007598 A1 | 1/2003 | Wang |
| 2003/0018272 A1 | 1/2003 | Treado et al. |
| 2003/0026386 A1 | 2/2003 | Tang |
| 2003/0048260 A1 | 3/2003 | Matusis |
| 2003/0073895 A1 | 4/2003 | Nields et al. |
| 2003/0095624 A1 | 5/2003 | Eberhard et al. |
| 2003/0097055 A1 | 5/2003 | Yanof |
| 2003/0128893 A1 | 7/2003 | Castorina |
| 2003/0135115 A1 | 7/2003 | Burdette et al. |
| 2003/0169847 A1 | 9/2003 | Karellas |
| 2003/0194050 A1 | 10/2003 | Eberhard |
| 2003/0194121 A1 | 10/2003 | Eberhard et al. |
| 2003/0194124 A1 | 10/2003 | Suzuki et al. |
| 2003/0195433 A1 | 10/2003 | Turovskiy |
| 2003/0210254 A1 | 11/2003 | Doan |
| 2003/0212327 A1 | 11/2003 | Wang |
| 2003/0215120 A1 | 11/2003 | Uppaluri |
| 2004/0008809 A1 | 1/2004 | Webber |
| 2004/0008900 A1 | 1/2004 | Jabri et al. |
| 2004/0008901 A1 | 1/2004 | Avinash |
| 2004/0036680 A1 | 2/2004 | Davis |
| 2004/0047518 A1 | 3/2004 | Tiana |
| 2004/0052328 A1 | 3/2004 | Saboi |
| 2004/0064037 A1 | 4/2004 | Smith |
| 2004/0066884 A1 | 4/2004 | Claus |
| 2004/0066904 A1 | 4/2004 | Eberhard et al. |
| 2004/0070582 A1 | 4/2004 | Smith et al. |
| 2004/0077938 A1 | 4/2004 | Mark et al. |
| 2004/0081273 A1 | 4/2004 | Ning |
| 2004/0094167 A1 | 5/2004 | Brady |
| 2004/0101095 A1 | 5/2004 | Jing et al. |
| 2004/0109028 A1 | 6/2004 | Stern et al. |
| 2004/0109529 A1 | 6/2004 | Eberhard et al. |
| 2004/0127789 A1 | 7/2004 | Ogawa |
| 2004/0138569 A1 | 7/2004 | Grunwald |
| 2004/0171933 A1 | 9/2004 | Stoller et al. |

(56) References Cited

U.S. PATENT DOCUMENTS

| | | |
|---|---|---|
| 2004/0171986 A1 | 9/2004 | Tremaglio, Jr. et al. |
| 2004/0267157 A1 | 12/2004 | Miller et al. |
| 2005/0047636 A1 | 3/2005 | Gines et al. |
| 2005/0049521 A1 | 3/2005 | Miller et al. |
| 2005/0063509 A1 | 3/2005 | Defreitas et al. |
| 2005/0078797 A1 | 4/2005 | Danielsson et al. |
| 2005/0084060 A1 | 4/2005 | Seppi et al. |
| 2005/0089205 A1 | 4/2005 | Kapur |
| 2005/0105679 A1 | 5/2005 | Wu et al. |
| 2005/0107689 A1 | 5/2005 | Sasano |
| 2005/0111718 A1 | 5/2005 | MacMahon |
| 2005/0113680 A1 | 5/2005 | Ikeda et al. |
| 2005/0113681 A1 | 5/2005 | DeFreitas et al. |
| 2005/0113715 A1 | 5/2005 | Schwindt et al. |
| 2005/0124845 A1 | 6/2005 | Thomadsen et al. |
| 2005/0135555 A1 | 6/2005 | Claus |
| 2005/0135664 A1 | 6/2005 | Kaufhold |
| 2005/0226375 A1 | 10/2005 | Eberhard |
| 2006/0004278 A1 | 1/2006 | Giger et al. |
| 2006/0009693 A1 | 1/2006 | Hanover et al. |
| 2006/0018526 A1 | 1/2006 | Avinash |
| 2006/0025680 A1 | 2/2006 | Jeune-Lomme |
| 2006/0030784 A1 | 2/2006 | Miller et al. |
| 2006/0074288 A1 | 4/2006 | Kelly et al. |
| 2006/0098855 A1 | 5/2006 | Gkanatsios et al. |
| 2006/0129062 A1 | 6/2006 | Nicoson et al. |
| 2006/0132508 A1 | 6/2006 | Sadikali |
| 2006/0147099 A1 | 7/2006 | Marshall et al. |
| 2006/0154267 A1 | 7/2006 | Ma et al. |
| 2006/0155209 A1 | 7/2006 | Miller et al. |
| 2006/0197753 A1 | 9/2006 | Hotelling |
| 2006/0210131 A1 | 9/2006 | Wheeler |
| 2006/0228012 A1 | 10/2006 | Masuzawa |
| 2006/0238546 A1 | 10/2006 | Handley |
| 2006/0257009 A1 | 11/2006 | Wang |
| 2006/0269040 A1 | 11/2006 | Mertelmeier |
| 2006/0274928 A1 | 12/2006 | Collins et al. |
| 2006/0291618 A1 | 12/2006 | Eberhard et al. |
| 2007/0014468 A1 | 1/2007 | Gines et al. |
| 2007/0019846 A1 | 1/2007 | Bullitt et al. |
| 2007/0030949 A1 | 2/2007 | Jing et al. |
| 2007/0036265 A1 | 2/2007 | Jing et al. |
| 2007/0046649 A1 | 3/2007 | Reiner |
| 2007/0047793 A1 | 3/2007 | Wu et al. |
| 2007/0052700 A1 | 3/2007 | Wheeler et al. |
| 2007/0076844 A1 | 4/2007 | Defreitas et al. |
| 2007/0114424 A1 | 5/2007 | Danielsson et al. |
| 2007/0118400 A1 | 5/2007 | Morita et al. |
| 2007/0156451 A1 | 7/2007 | Gering |
| 2007/0223651 A1 | 9/2007 | Wagenaar et al. |
| 2007/0225600 A1 | 9/2007 | Weibrecht et al. |
| 2007/0236490 A1 | 10/2007 | Casteele |
| 2007/0242800 A1 | 10/2007 | Jing et al. |
| 2007/0263765 A1 | 11/2007 | Wu |
| 2007/0274585 A1 | 11/2007 | Zhang et al. |
| 2008/0019581 A1 | 1/2008 | Gkanatsios et al. |
| 2008/0043905 A1 | 2/2008 | Hassanpourgol |
| 2008/0045833 A1 | 2/2008 | DeFreitas et al. |
| 2008/0101537 A1 | 5/2008 | Sendai |
| 2008/0114614 A1 | 5/2008 | Mahesh et al. |
| 2008/0125643 A1 | 5/2008 | Huisman |
| 2008/0130979 A1 | 6/2008 | Ren |
| 2008/0139896 A1 | 6/2008 | Baumgart |
| 2008/0152086 A1 | 6/2008 | Hall |
| 2008/0165136 A1 | 7/2008 | Christie et al. |
| 2008/0187095 A1 | 8/2008 | Boone et al. |
| 2008/0198966 A1 | 8/2008 | Hjarn |
| 2008/0221479 A1 | 9/2008 | Ritchie |
| 2008/0229256 A1 | 9/2008 | Shibaike |
| 2008/0240533 A1 | 10/2008 | Piron et al. |
| 2008/0297482 A1 | 12/2008 | Weiss |
| 2009/0003519 A1 | 1/2009 | DeFreitas |
| 2009/0005668 A1 | 1/2009 | West et al. |
| 2009/0005693 A1 | 1/2009 | Brauner |
| 2009/0010384 A1 | 1/2009 | Jing et al. |
| 2009/0034684 A1 | 2/2009 | Bernard |
| 2009/0037821 A1 | 2/2009 | O'Neal et al. |
| 2009/0063118 A1 | 3/2009 | Dachille et al. |
| 2009/0079705 A1 | 3/2009 | Sizelove et al. |
| 2009/0080594 A1 | 3/2009 | Brooks et al. |
| 2009/0080602 A1 | 3/2009 | Brooks et al. |
| 2009/0080604 A1 | 3/2009 | Shores et al. |
| 2009/0080752 A1 | 3/2009 | Ruth |
| 2009/0080765 A1 | 3/2009 | Bernard et al. |
| 2009/0087067 A1 | 4/2009 | Khorasani |
| 2009/0123052 A1 | 5/2009 | Ruth |
| 2009/0129644 A1 | 5/2009 | Daw et al. |
| 2009/0135997 A1 | 5/2009 | Defreitas et al. |
| 2009/0138280 A1 | 5/2009 | Morita et al. |
| 2009/0143674 A1 | 6/2009 | Nields |
| 2009/0167702 A1 | 7/2009 | Nurmi |
| 2009/0171244 A1 | 7/2009 | Ning |
| 2009/0238424 A1 | 9/2009 | Arakita |
| 2009/0259958 A1 | 10/2009 | Ban |
| 2009/0268865 A1 | 10/2009 | Ren et al. |
| 2009/0278812 A1 | 11/2009 | Yasutake |
| 2009/0296882 A1 | 12/2009 | Gkanatsios et al. |
| 2009/0304147 A1 | 12/2009 | Jing et al. |
| 2010/0034348 A1 | 2/2010 | Yu |
| 2010/0049046 A1 | 2/2010 | Peiffer |
| 2010/0054400 A1 | 3/2010 | Ren et al. |
| 2010/0067648 A1 | 3/2010 | Kojima |
| 2010/0079405 A1 | 4/2010 | Bernstein |
| 2010/0086188 A1 | 4/2010 | Ruth et al. |
| 2010/0088346 A1 | 4/2010 | Urness et al. |
| 2010/0098214 A1 | 4/2010 | Star-Lack et al. |
| 2010/0105879 A1 | 4/2010 | Katayose et al. |
| 2010/0121178 A1 | 5/2010 | Krishnan |
| 2010/0131294 A1 | 5/2010 | Venon |
| 2010/0131482 A1 | 5/2010 | Linthicum et al. |
| 2010/0135558 A1 | 6/2010 | Ruth et al. |
| 2010/0152570 A1 | 6/2010 | Navab |
| 2010/0166147 A1 | 7/2010 | Abenaim |
| 2010/0166267 A1 | 7/2010 | Zhang |
| 2010/0171764 A1 | 7/2010 | Feng et al. |
| 2010/0189322 A1 | 7/2010 | Sakagawa |
| 2010/0195882 A1 | 8/2010 | Ren et al. |
| 2010/0208037 A1 | 8/2010 | Sendai |
| 2010/0231522 A1 | 9/2010 | Li |
| 2010/0246884 A1 | 9/2010 | Chen et al. |
| 2010/0246909 A1 | 9/2010 | Blum |
| 2010/0259561 A1 | 10/2010 | Forutanpour et al. |
| 2010/0259645 A1 | 10/2010 | Kaplan |
| 2010/0260316 A1 | 10/2010 | Stein et al. |
| 2010/0280375 A1 | 11/2010 | Zhang |
| 2010/0293500 A1 | 11/2010 | Cragun |
| 2011/0018817 A1 | 1/2011 | Kryze |
| 2011/0019891 A1 | 1/2011 | Puong |
| 2011/0054944 A1 | 3/2011 | Sandberg et al. |
| 2011/0069808 A1 | 3/2011 | Defreitas et al. |
| 2011/0069906 A1 | 3/2011 | Park |
| 2011/0087132 A1 | 4/2011 | DeFreitas et al. |
| 2011/0105879 A1 | 5/2011 | Masumoto |
| 2011/0109650 A1 | 5/2011 | Kreeger |
| 2011/0110570 A1 | 5/2011 | Bar-Shalev |
| 2011/0110576 A1 | 5/2011 | Kreeger |
| 2011/0123073 A1 | 5/2011 | Gustafson |
| 2011/0125526 A1 | 5/2011 | Gustafson |
| 2011/0134113 A1 | 6/2011 | Ma et al. |
| 2011/0150447 A1 | 6/2011 | Li |
| 2011/0157154 A1 | 6/2011 | Bernard et al. |
| 2011/0163939 A1 | 7/2011 | Tam et al. |
| 2011/0178389 A1 | 7/2011 | Kumar et al. |
| 2011/0182402 A1 | 7/2011 | Partain |
| 2011/0234630 A1 | 9/2011 | Batman et al. |
| 2011/0237927 A1 | 9/2011 | Brooks et al. |
| 2011/0242092 A1 | 10/2011 | Kashiwagi |
| 2011/0310126 A1 | 12/2011 | Georgiev et al. |
| 2012/0014501 A1 | 1/2012 | Pelc |
| 2012/0014504 A1 | 1/2012 | Jang |
| 2012/0014578 A1 | 1/2012 | Karssemeijer |
| 2012/0069951 A1 | 3/2012 | Toba |
| 2012/0106698 A1 | 5/2012 | Karim |
| 2012/0127297 A1 | 5/2012 | Baxi |

(56) References Cited

U.S. PATENT DOCUMENTS

| | | |
|---|---|---|
| 2012/0131488 A1 | 5/2012 | Karlsson et al. |
| 2012/0133600 A1 | 5/2012 | Marshall |
| 2012/0133601 A1 | 5/2012 | Marshall |
| 2012/0134464 A1 | 5/2012 | Hoernig et al. |
| 2012/0148151 A1 | 6/2012 | Hamada |
| 2012/0150034 A1 | 6/2012 | DeFreitas et al. |
| 2012/0189092 A1 | 7/2012 | Jerebko |
| 2012/0194425 A1 | 8/2012 | Buelow |
| 2012/0238870 A1 | 9/2012 | Smith et al. |
| 2012/0277625 A1 | 11/2012 | Nakayama |
| 2012/0293511 A1 | 11/2012 | Mertelmeier |
| 2013/0016255 A1 | 1/2013 | Bhatt |
| 2013/0022165 A1 | 1/2013 | Jang |
| 2013/0044861 A1 | 2/2013 | Muller |
| 2013/0059758 A1 | 3/2013 | Haick |
| 2013/0108138 A1 | 5/2013 | Nakayama |
| 2013/0121569 A1 | 5/2013 | Yadav |
| 2013/0121618 A1 | 5/2013 | Yadav |
| 2013/0202168 A1 | 8/2013 | Jerebko |
| 2013/0259193 A1 | 10/2013 | Packard |
| 2014/0033126 A1 | 1/2014 | Kreeger |
| 2014/0035811 A1 | 2/2014 | Guehring |
| 2014/0064444 A1 | 3/2014 | Oh |
| 2014/0073913 A1 | 3/2014 | DeFreitas et al. |
| 2014/0082542 A1 | 3/2014 | Zhang et al. |
| 2014/0200433 A1 | 7/2014 | Choi |
| 2014/0219534 A1 | 8/2014 | Wiemker et al. |
| 2014/0219548 A1 | 8/2014 | Wels |
| 2014/0276061 A1 | 9/2014 | Lee et al. |
| 2014/0327702 A1 | 11/2014 | Kreeger et al. |
| 2014/0328517 A1 | 11/2014 | Gluncic |
| 2015/0004558 A1 | 1/2015 | Inglese |
| 2015/0052471 A1 | 2/2015 | Chen |
| 2015/0061582 A1 | 4/2015 | Smith |
| 2015/0238148 A1 | 8/2015 | Georgescu |
| 2015/0258271 A1 | 9/2015 | Love |
| 2015/0302146 A1 | 10/2015 | Marshall |
| 2015/0309712 A1 | 10/2015 | Marshall |
| 2015/0317538 A1 | 11/2015 | Ren et al. |
| 2015/0331995 A1 | 11/2015 | Zhao |
| 2016/0000399 A1 | 1/2016 | Halmann et al. |
| 2016/0022364 A1 | 1/2016 | DeFreitas et al. |
| 2016/0051215 A1 | 2/2016 | Chen |
| 2016/0078645 A1 | 3/2016 | Abdurahman |
| 2016/0140749 A1 | 5/2016 | Erhard |
| 2016/0210774 A1 | 7/2016 | Wiskin et al. |
| 2016/0228034 A1 | 8/2016 | Gluncic |
| 2016/0235380 A1 | 8/2016 | Smith |
| 2016/0350933 A1 | 12/2016 | Schieke |
| 2016/0364526 A1 | 12/2016 | Reicher et al. |
| 2016/0367210 A1 | 12/2016 | Gkanatsios |
| 2017/0071562 A1 | 3/2017 | Suzuki |
| 2017/0132792 A1 | 5/2017 | Jerebko et al. |
| 2017/0202453 A1 | 7/2017 | Sekiguchi |
| 2017/0262737 A1 | 9/2017 | Rabinovich |
| 2018/0008220 A1 | 1/2018 | Boone et al. |
| 2018/0008236 A1 | 1/2018 | Venkataraman et al. |
| 2018/0047211 A1 | 2/2018 | Chen et al. |
| 2018/0109698 A1 | 4/2018 | Ramsay et al. |
| 2018/0132722 A1 | 5/2018 | Eggers et al. |
| 2018/0137385 A1 | 5/2018 | Ren |
| 2018/0144244 A1 | 5/2018 | Masoud |
| 2018/0256118 A1 | 9/2018 | DeFreitas |
| 2019/0000318 A1 | 1/2019 | Caluser |
| 2019/0015173 A1 | 1/2019 | DeFreitas |
| 2019/0037173 A1 | 1/2019 | Lee et al. |
| 2019/0043456 A1 | 2/2019 | Kreeger |
| 2019/0057778 A1 | 2/2019 | Porter et al. |
| 2019/0287241 A1 | 9/2019 | Hill et al. |
| 2019/0290221 A1 | 9/2019 | Smith |
| 2019/0325573 A1 | 10/2019 | Bernard et al. |
| 2020/0046303 A1 | 2/2020 | DeFreitas |
| 2020/0054300 A1 | 2/2020 | Kreeger et al. |
| 2020/0093562 A1 | 3/2020 | DeFreitas |
| 2020/0184262 A1 | 6/2020 | Chui |
| 2020/0205928 A1 | 7/2020 | DeFreitas |
| 2020/0253573 A1 | 8/2020 | Gkanatsios |
| 2020/0345320 A1 | 11/2020 | Chen |
| 2021/0100518 A1 | 4/2021 | Chui |
| 2021/0113167 A1 | 4/2021 | Chui |
| 2021/0118199 A1 | 4/2021 | Chui |
| 2021/0174504 A1 | 6/2021 | Madabhushi |
| 2021/0212665 A1 | 7/2021 | Tsymbalenko |
| 2022/0005277 A1 | 1/2022 | Chen |
| 2022/0013089 A1 | 1/2022 | Kreeger |
| 2022/0036545 A1 | 2/2022 | St. Pierre |
| 2022/0192615 A1 | 6/2022 | Chui |
| 2022/0254023 A1 | 8/2022 | McKinney et al. |
| 2022/0386969 A1 | 12/2022 | Smith |
| 2023/0000467 A1 | 1/2023 | Shi |
| 2023/0038498 A1 | 2/2023 | Xu |
| 2023/0053489 A1 | 2/2023 | Kreeger |
| 2023/0054121 A1 | 2/2023 | Chui |
| 2023/0056692 A1 | 2/2023 | Gkanatsios |
| 2023/0082494 A1 | 3/2023 | Chui |
| 2023/0098305 A1 | 3/2023 | St. Pierre |
| 2023/0103969 A1 | 4/2023 | St. Pierre |
| 2023/0124481 A1 | 4/2023 | St. Pierre |
| 2023/0125385 A1 | 4/2023 | Solis |
| 2023/0344453 A1 | 10/2023 | Yang |
| 2024/0169958 A1 | 5/2024 | Kreeger |
| 2024/0315654 A1 | 9/2024 | Chui |
| 2024/0320827 A1 | 9/2024 | Chui |

FOREIGN PATENT DOCUMENTS

| | | |
|---|---|---|
| CN | 1846622 | 10/2006 |
| CN | 101066212 A | 11/2007 |
| CN | 102169530 A | 8/2011 |
| CN | 202161328 | 3/2012 |
| CN | 102429678 | 5/2012 |
| CN | 102473300 A | 5/2012 |
| CN | 105193447 | 12/2015 |
| CN | 106659468 A | 5/2017 |
| CN | 107440730 | 12/2017 |
| CN | 112561908 A | 3/2021 |
| DE | 102010009295 | 8/2011 |
| DE | 102011087127 | 5/2013 |
| EP | 775467 | 5/1997 |
| EP | 982001 | 3/2000 |
| EP | 1428473 | 6/2004 |
| EP | 2236085 | 6/2010 |
| EP | 2215600 | 8/2010 |
| EP | 2301432 | 3/2011 |
| EP | 2491863 | 8/2012 |
| EP | 1986548 | 1/2013 |
| EP | 2656789 | 10/2013 |
| EP | 2823464 | 1/2015 |
| EP | 2823765 | 1/2015 |
| EP | 2889743 | 7/2015 |
| EP | 3060132 | 4/2019 |
| JP | H09-35043 | 2/1997 |
| JP | H09-198490 | 7/1997 |
| JP | H09-238934 | 9/1997 |
| JP | H10-33523 | 2/1998 |
| JP | 2000-200340 | 7/2000 |
| JP | 2002-109510 | 4/2002 |
| JP | 2002-282248 | 10/2002 |
| JP | 2003-126073 | 5/2003 |
| JP | 2003-189179 | 7/2003 |
| JP | 2003-199737 | 7/2003 |
| JP | 2003-531516 | 10/2003 |
| JP | 2004254742 | 9/2004 |
| JP | 2005-110843 | 4/2005 |
| JP | 2005-522305 | 7/2005 |
| JP | 2005-227350 | 8/2005 |
| JP | 2005-322257 | 11/2005 |
| JP | 2006-519634 | 8/2006 |
| JP | 2006-312026 | 11/2006 |
| JP | 2007-130487 | 5/2007 |
| JP | 2007-216022 | 8/2007 |
| JP | 2007-325928 | 12/2007 |
| JP | 2007-330334 | 12/2007 |
| JP | 2007-536968 | 12/2007 |

(56) References Cited

FOREIGN PATENT DOCUMENTS

| | | |
|---|---|---|
| JP | 2008-068032 | 3/2008 |
| JP | 2008518684 | 6/2008 |
| JP | 2008-253401 | 10/2008 |
| JP | 2009-034503 | 2/2009 |
| JP | 2009-522005 | 6/2009 |
| JP | 2009-526618 | 7/2009 |
| JP | 2009-207545 | 9/2009 |
| JP | 2010-137004 | 6/2010 |
| JP | 2011-110175 A | 6/2011 |
| JP | 2012-011255 | 1/2012 |
| JP | 2012-501750 | 1/2012 |
| JP | 2012-061196 | 3/2012 |
| JP | 2013-530768 | 8/2013 |
| JP | 2013-244211 | 12/2013 |
| JP | 2014-507250 | 3/2014 |
| JP | 2014-534042 | 12/2014 |
| JP | 2015-506794 | 3/2015 |
| JP | 2015-144632 A | 8/2015 |
| JP | 2016-198197 | 12/2015 |
| JP | 2016059743 | 4/2016 |
| JP | 2017-000364 | 1/2017 |
| JP | 2017-056358 | 3/2017 |
| KR | 10-2015-0010515 | 1/2015 |
| KR | 10-2017-0062839 | 6/2017 |
| WO | 90/05485 | 5/1990 |
| WO | 93/17620 | 9/1993 |
| WO | 94/06352 | 3/1994 |
| WO | 1997/00649 | 1/1997 |
| WO | 1998/16903 | 4/1998 |
| WO | 00/51484 | 9/2000 |
| WO | 2003/020114 | 3/2003 |
| WO | 03/077202 | 9/2003 |
| WO | 2005051197 | 6/2005 |
| WO | 2005/110230 | 11/2005 |
| WO | 2005/112767 | 12/2005 |
| WO | 2006/055830 | 5/2006 |
| WO | 2006/058160 | 6/2006 |
| WO | 2007/095330 | 8/2007 |
| WO | 08/014670 | 2/2008 |
| WO | 2008047270 | 4/2008 |
| WO | 2008/050823 | 5/2008 |
| WO | 2008/054436 | 5/2008 |
| WO | 2009/026587 | 2/2009 |
| WO | 2010/028208 | 3/2010 |
| WO | 2010059920 | 5/2010 |
| WO | 2011008239 | 1/2011 |
| WO | 2011/043838 | 4/2011 |
| WO | 2011065950 | 6/2011 |
| WO | 2011073864 | 6/2011 |
| WO | 2011091300 | 7/2011 |
| WO | 2012/001572 | 1/2012 |
| WO | 2012/068373 | 5/2012 |
| WO | 2012063653 | 5/2012 |
| WO | 2012/112627 | 8/2012 |
| WO | 2012/122399 | 9/2012 |
| WO | 2013/001439 | 1/2013 |
| WO | 2013/035026 | 3/2013 |
| WO | 2013/078476 | 5/2013 |
| WO | 2013/123091 | 8/2013 |
| WO | 2013/136222 | 9/2013 |
| WO | 2014/080215 | 5/2014 |
| WO | 2014/149554 | 9/2014 |
| WO | 2014/207080 | 12/2014 |
| WO | 2015/061582 | 4/2015 |
| WO | 2015/066650 | 5/2015 |
| WO | 2015/130916 | 9/2015 |
| WO | 2016/103094 | 6/2016 |
| WO | 2016/184746 | 11/2016 |
| WO | 2016/206942 | 12/2016 |
| WO | 2018/183548 | 10/2018 |
| WO | 2018/183549 | 10/2018 |
| WO | 2018/183550 | 10/2018 |
| WO | 2018/236565 | 12/2018 |
| WO | 2019/032558 | 2/2019 |
| WO | 2019/091807 | 5/2019 |
| WO | 2021/021329 | 2/2021 |
| WO | 2021/168281 | 8/2021 |
| WO | 2021/195084 | 9/2021 |

OTHER PUBLICATIONS

"Supersonic to feature Aixplorer Ultimate at ECR", AuntiMinnie.com, 3 pages (Feb. 2018).

Al Sallab et al., "Self Learning Machines Using Deep Networks", Soft Computing and Pattern Recognition (SoCPaR), 2011 Int'l. Conference of IEEE, Oct. 14, 2011, pp. 21-26.

Berg, Wa et al., "Combined screening with ultrasound and mammography vs mammography alone in women at elevated risk of breast cancer", JAMA 299:2151-2163, 2008.

Burbank, Fred, "Stereotactic Breast Biopsy: Its History, Its Present, and Its Future", published in 1996 at the Southeastern Surgical Congress, 24 pages.

Bushberg, Jerrold et al., "The Essential Physics of Medical Imaging", 3rd ed., in: "The Essential Physics of Medical Imaging, Third Edition", Dec. 28, 2011, Lippincott & Wilkins, Philadelphia, PA, USA, XP05579051, pp. 270-272.

Canadian Office Action in Application 2829349, mailed Oct. 15, 2018, 4 pages.

Caroline, B.E. et al., "Computer aided detection of masses in digital breast tomosynthesis: a review", 2012 International Conference on Emerging Trends in Science, Engineering and Technology (INCOSET), Tiruchirappalli, 2012, pp. 186-191.

Carton, AK, et al., "Dual-energy contrast-enhanced digital breast tomosynthesis—a feasibility study", BR J Radiol. Apr. 2010;83 (988):344-50.

Chan, Heang-Ping et al., "Computer-aided detection system for breast masses on digital tomosynthesis mammograms: Preliminary Experience", Radiology, Dec. 2005, 1075-1080.

Chan, Heang-Ping et al., "ROC Study of the effect of stereoscopic imaging on assessment of breast lesions," Medical Physics, vol. 32, No. 4, Apr. 2005, 1001-1009.

Chen, SC, et al., "Initial clinical experience with contrast-enhanced digital breast tomosynthesis", Acad Radio. Feb. 2007 14(2):229-38.

Chinese 2nd Office Action in Application 201480058064.5, mailed Jul. 16, 2019, 5 pgs.

Cho, N. et al., "Distinguishing Benign from Malignant Masses at Breast US: Combined US Elastography and Color Doppler US-Influence on Radiologist Accuracy", Radiology, 262(1): 80-90 (Jan. 2012).

Conner, Peter, "Breast Response to Menopausal Hormone Therapy—Aspects on Proliferation, apoptosis and Mammographic Density", 2007 Annals of Medicine, 39;1, 28-41.

Diekmann, Felix et al., "Thick Slices from Tomosynthesis Data Sets: Phantom Study for the Evaluation of Different Algorithms", Journal of Digital Imaging, Springer, vol. 22, No. 5, Oct. 23, 2007, pp. 519-526.

Diekmann, Felix., et al., "Digital mammography using iodine-based contrast media: initial clinical experience with dynamic contrast medium enhancement", Invest Radiol 2005; 40:397-404.

Dromain C., et al., "Contrast enhanced spectral mammography: a multi-reader study", RSNA 2010, 96th Scientific Assembly and Scientific Meeting.

Dromain, C., et al., "Contrast-enhanced digital mammography", Eur J Radiol. 2009; 69:34-42.

Dromain, Clarisse et al., "Dual-energy contrast-enhanced digital mammography: initial clinical results", European Radiology, Sep. 14, 2010, vol. 21, pp. 565-574.

Dromain, Clarisse, et al., "Evaluation of tumor angiogenesis of breast carcinoma using contrast-enhanced digital mammography", AJR: 187, Nov. 2006, 16 pages.

Duan, Xiaoman et al., "Matching corresponding regions of interest on cranio-caudal and medio-lateral oblique view mammograms", IEEE Access, vol. 7, Mar. 25, 2019, pp. 31586-31597, XP011715754, DOI: 10.1109/Access.2019.2902854, retrieved on Mar. 20, 2019, abstract.

(56) References Cited

OTHER PUBLICATIONS

E. Shaw de Paredes et al., "Interventional Breast Procedure", published Sep/Oct. 1998 in Curr Probl Diagn Radiol, pp. 138-184. (D15 in oppo).

EFilm Mobile HD by Merge Healthcare, web site: http://itunes.apple.com/bw/app/efilm-mobile-hd/id405261243?mt=8, accessed on Nov. 3, 2011 (2 pages).

EFilm Solutions, eFilm Workstation (tm) 3.4, website: http://estore.merge.com/na/estore/content.aspx?productID=405, accessed on Nov. 3, 2011 (2 pages).

Elbakri, Idris A. et al., "Automatic exposure control for a slot scanning full field digital mammography system", Med. Phys. 2005; Sep. 32(9):2763-2770, Abstract only.

Ertas, M. et al., "2D versus 3D total variation minimization in digital breast tomosynthesis", 2015 IEEE International Conference on Imaging Systems and Techniques (IST), Macau, 2015, pp. 1-4.

European Communication in Application 10707751.3, mailed Oct. 4, 2018, 5 pages.

European Communication in Application 10707751.3, mailed Aug. 7, 2019, 6 pages.

European Extended Search Report dated Jul. 18, 2014 in EP App 12754521.8, 7 pages.

European Extended Search Report for European Patent Application No. 14770362.3 mailed Sep. 28, 2016, 8 pgs.

European Extended Search Report in Application 14855181.5, mailed May 15, 2017, 7 pages.

European extended Search Report in Application 18153706.9, mailed Jun. 1, 2018, 8 pages.

European Mar. 23, 2009 European Search Report in connection with counterpart European patent Application No. 07750818.

European Office Action in Application 10707751.3, mailed Feb. 19, 2018, 5 pgs.

Feng, Steve Si Jia, et al., "Clinical digital breast tomosynthesis system: Dosimetric Characterization", Radiology, Apr. 2012, 263(1); pp. 35-42.

Fischer Imaging Corp, Mammotest Plus manual on minimally invasive breast biopsy system, 2002, 8 pages.

Fischer Imaging Corporation, Installation Manual, MammoTest Family of Breast Biopsy Systems, 86683G, 86684G, P-55957-IM, Issue 1, Revision 3, Jul. 2005, 98 pages.

Fischer Imaging Corporation, Operator Manual, MammoTest Family of Breast Biopsy Systems, 86683G, 86684G, P-55956-OM, Issue 1, Revision 6, Sep. 2005, 258 pages.

Freiherr, G., "Breast tomosynthesis trials show promise", Diagnostic Imaging—San Francisco 2005, V27; N4:42-48.

Georgian-Smith, Dianne, et al., "Stereotactic Biopsy of the Breast Using an Upright Unit, a Vacuum-Suction Needle, and a Lateral Arm-Support System", 2001, at the American Roentgen Ray Society meeting, 8 pages.

Ghiassi, M. et al., "A Dynamic Architecture for Artificial Networks", Neurocomputing, vol. 63, Aug. 20, 2004, pp. 397-413.

Giger et al. "Development of a smart workstation for use in mammography", in Proceedings of SPIE, vol. 1445 (1991), pp. 101103; 4 pages.

Giger et al., "An Intelligent Workstation for Computer-aided Diagnosis", in RadioGraphics, May 1993, 13:3 pp. 647-656; 10 pages.

Glick, Stephen J., "Breast CT", Annual Rev. Biomed. Eng., 2007, 9;501-26.

Green, C. et al., "Deformable mapping using biochemical models to relate corresponding lesions in digital breast tomosynthesis and automated breast ultrasound images", Medical Image Analysis, 60: 1-18 (Nov. 2019).

Hologic, "Lorad StereoLoc II" Operator's Manual 9-500-0261, Rev. 005, 2004, 78 pgs.

Hologic, Inc., 510(k) Summary, prepared Nov. 28, 2010, for Affirm Breast Biopsy Guidance System Special 510(k) Premarket Notification, 5 pages.

Hologic, Inc., 510(k) Summary, prepared Aug. 14, 2012, for Affirm Breast Biopsy Guidance System Special 510(k) Premarket Notification, 5 pages.

ICRP Publication 60: 1990 Recommendations of the International Commission on Radiological Protection, 12 pages.

Ijaz, Umer Zeeshan, et al., "Mammography phantom studies using 3D electrical impedance tomography with numerical forward solver", Frontiers in the Convergence of Bioscience and Information Technologies 2007, 379-383.

Japanese Notice of Final Rejection in Application 2016-526115, mailed Jun. 24, 2019, 5 pages.

Jochelson, M., et al., "Bilateral Dual Energy contrast-enhanced digital mammography: Initial Experience", RSNA 2010, 96th Scientific Assembly and Scientific Meeting, 1 page.

Jong, RA, et al., Contrast-enhanced digital mammography: initial clinical experience. Radiology 2003; 228:842-850.

Kao, Tzu-Jen et al., "Regional admittivity spectra with tomosynthesis images for breast cancer detection", Proc. of the 29th Annual Int'l. Conf. of the IEEE EMBS, Aug. 23-26, 2007, 4142-4145.

Kim, Eun Sil, et al., "Significance of microvascular evaluation of ductal lesions on breast ultrasonography: Influence on diagnostic performance", Clinical Imaging, Elsevier, NY, vol. 51, Jun. 6, 2018, pp. 252-259.

Koechli, Ossi R., "Available Sterotactic Systems for Breast Biopsy", Renzo Brun del Re (Ed.), Minimally Invasive Breast Biopsies, Recent Results in Cancer Research 173:105-113; Springer-Verlag, 2009.

Kopans, Daniel B., "Breast Imaging", 3rd Edition, Lippincott Williams and Wilkins, published Nov. 2, 2006, pp. 960-967.

Kopans, et al. Will tomosynthesis replace conventional mammography? Plenary Session SFN08: RSNA 2005.

Lee, E. et al., "Combination of Quantitative Parameters of Shear Wave Elastography and Superb Microvascular Imaging to Evaluate Breast Masses", Korean Journal of Radiology: Official Journal of the Korean Radiological Society, 21(9): 1045-1054 (Jan. 2020).

Lehman, CD, et al. MRI evaluation of the contralateral breast in women with recently diagnosed breast cancer. N Engl J Med 2007; 356: 1295-1303.

Lewin,JM, et al., Dual-energy contrast-enhanced digital subtraction mammography: feasibility. Radiology 2003; 229:261-268.

Lilja, Mikko, "Fast and accurate voxel projection technique in free-form cone-beam geometry with application to algebraic reconstruction," Applies Sciences on Biomedical and Communication Technologies, 2008, Isabel '08, first international symposium on, IEEE, Piscataway, NJ, Oct. 25, 2008.

Lindfors, KK, et al., Dedicated breast CT: initial clinical experience. Radiology 2008; 246(3): 725-733.

Love, Susan M., et al. "Anatomy of the nipple and breast ducts revisited", Cancer, American Cancer Society, Philadelphia, PA, vol. 101, No. 9, Sep. 20, 2004, pp. 1947-1957.

Mahesh, Mahadevappa, "AAPM/RSNA Physics Tutorial for Residents—Digital Mammography: an Overview", Nov-Dec. 2004, vol. 24, No. 6, 1747-1760.

Metheany, Kathrine G. et al., "Characterizing anatomical variability in breast CT images", Oct. 2008, Med. Phys. 35 (10); 4685-4694.

Niklason, L., et al., Digital tomosynthesis in breast imaging. Radiology. Nov. 1997; 205(2):399-406.

Nikunjc, Oza et al., Dietterich, T.G., Ed., "Ensemble methods in machine learning", Jan. 1, 2005, Multiple Classifier Systems, Lecture Notes in Computer Science; LNCS, Springer-Verlag Berlin/Heidelberg, pp. 1-15, abstract.

Observations by Third Party, Remarks concerning European patent application No. 10707751.3 according to Article 115 EPC, dated Apr. 24, 2014, 8 pgs.

Pathmanathan et al., "Predicting tumour location by simulating large deformations of the breast using a 3D finite element model and nonlinear elasticity", Medical Image Computing and Computer-Assisted Intervention, pp. 217-224, vol. 3217 (2004).

PCT Feb. 20, 2008 International Search Report and Written Opinion in connection with corresponding International patent application No. PCT/US2007/04006, 7 pgs.

PCT International Preliminary Report on Patentability in International Application PCT/US2014/061994, mailed Apr. 26, 2016, 5 pages.

PCT International Search Report and Written Opinion in Application PCT/US2010/025873, dated Aug. 2, 2010, 19 pgs.

(56) References Cited

OTHER PUBLICATIONS

PCT International Search Report in Application PCT/US2014/026164, mailed Jul. 28, 2014, 1 page.
PCT International Written Report for International Application PCT/US2014/026164, mailed Jul. 28, 2014, 2 pgs.
PCT Written Opinion in International Application PCT/US2014/061994, mailed Jan. 22, 2015, 4 pages.
PCT/US12/28334 International Search Report and Written Opinion, dated Jul. 5, 2012, 7 pages.
Pediconi, "Color-coded automated signal intensity-curve for detection and characterization of breast lesions: Preliminary evaluation of new software for MR-based breast imaging," International Congress Series 1281 (2005) 1081-1086.
Poplack, SP, et al., Digital breast tomosynthesis: initial experience in 98 women with abnormal digital screening mammography. AJR Am J Roentgenology Sep. 2007 189(3):616-23.
Prionas, ND, et al., Contrast-enhanced dedicated breast CT: initial clinical experience. Radiology. Sep. 2010 256(3):714-723.
Rafferty, E. et al., "Assessing Radiologist Performance Using Combined Full-Field Digital Mammography and Breast Tomosynthesis Versus Full-Field Digital Mammography Alone: Results" . . . presented at 2007 Radiological Society of North America meeting, Chicago IL.
Reynolds, April, "Stereotactic Breast Biopsy: a Review", Radiologic Technology, vol. 80, No. 5, Jun. 1, 2009, pp. 447M-464M, XP055790574.
Sakic et al., "Mammogram synthesis using a 3D simulation. I. breast tissue model and image acquisition simulation" Medical Physics. 29, pp. 2131-2139 (2002).
Samani, A. et al., "Biomechanical 3-D Finite Element Modeling of the Human Breast Using MRI Data", 2001, IEEE Transactions on Medical Imaging, vol. 20, No. 4, pp. 271-279.
Samulski, Maurice et al., "Optimizing case-based detection performance in a multiview CAD system for mammography", IEEE Transactions on Medical Imaging, vol. 30, No. 4, Apr. 1, 2011, pp. 1001-1009, XP011352387, ISSN: 0278-0062, DOI: 10.1109/TMI.2011.2105886, abstract.
Sechopoulos, et al., "Glandular radiation dose in tomosynthesis of the breast using tungsten targets", Journal of Applied Clinical Medical Physics, vol. 8, No. 4, Fall 2008, 161-171.
Shrading, Simone et al., "Digital Breast Tomosynthesis-guided Vacuum-assisted Breast Biopsy: Initial Experiences and Comparison with Prone Stereotactic Vacuum-assisted Biopsy", the Department of Diagnostic and Interventional Radiology, Univ. of Aachen, Germany, published Nov. 12, 2014, 10 pgs.
Smith, A., "Full field breast tomosynthesis", Radiol Manage. Sep.-Oct. 2005; 27(5):25-31.
Taghibakhsh, f. et al., "High dynamic range 2-TFT amplified pixel sensor architecture for digital mammography tomosynthesis", IET Circuits Devices Syst., 2007, 1(10, pp. 87-92.
Van Schie, Guido, et al., "Generating Synthetic Mammograms from Reconstructed Tomosynthesis Volumes", IEEE Transactions on Medical Imaging, vol. 32, No. 12, Dec. 2013, 2322-2331.
Van Schie, Guido, et al., "Mass detection in reconstructed digital breast tomosynthesis volumes with a computer-aided detection system trained on 2D mammograms", Med. Phys. 40(4), Apr. 2013, 41902-1-41902-11.
Varjonen, Mari, "Three-Dimensional Digital Breast Tomosynthesis in the Early Diagnosis and Detection of Breast Cancer", IWDM 2006, LNCS 4046, 152-159.
Weidner N, et al., "Tumor angiogenesis and metastasis: correlation in invasive breast carcinoma", New England Journal of Medicine 1991; 324:1-8.
Weidner, N, "The importance of tumor angiogenesis: the evidence continues to grow", Am J Clin Pathol. Nov. 2004 122(5):696-703.
Wen, Junhai et al., "A study on truncated cone-beam sampling strategies for 3D mammography", 2004, IEEE, 3200-3204.
Williams, Mark B. et al., "Optimization of exposure parameters in full field digital mammography", Medical Physics 35, 2414 (May 20, 2008); doi: 10.1118/1.2912177, pp. 2414-2423.
Wodajo, Felasfa, MD, "Now Playing: Radiology Images from Your Hospital PACS on your iPad," Mar. 17, 2010; web site: http://www.imedicalapps.com/2010/03/now-playing-radiology-images-from-your-hospital-pacs-on-your-ipad/, accessed on Nov. 3, 2011 (3 pages).
Yin, H.M., et al., "Image Parser: a tool for finite element generation from three-dimensional medical images", BioMedical Engineering Online. 3:31, pp. 1-9, Oct. 1, 2004.
Zhang, Yiheng et al., "A comparative study of limited-angle cone-beam reconstruction methods for breast tomosynthesis", Med Phys., Oct. 2006, 33(10): 3781-3795.
Zhao, Bo, et al., "Imaging performance of an amorphous selenium digital mammography detector in a breast tomosynthesis system", May 2008, Med. Phys 35(5); 1978-1987.

System showing side lateral needle access to area of interest

System showing front needle access to area of interest

System showing asymmetric tomo scan to avoid shadowing the gun stage

System showing tomo scan skipping exposures at angles that would cause artifacts of stage in the image

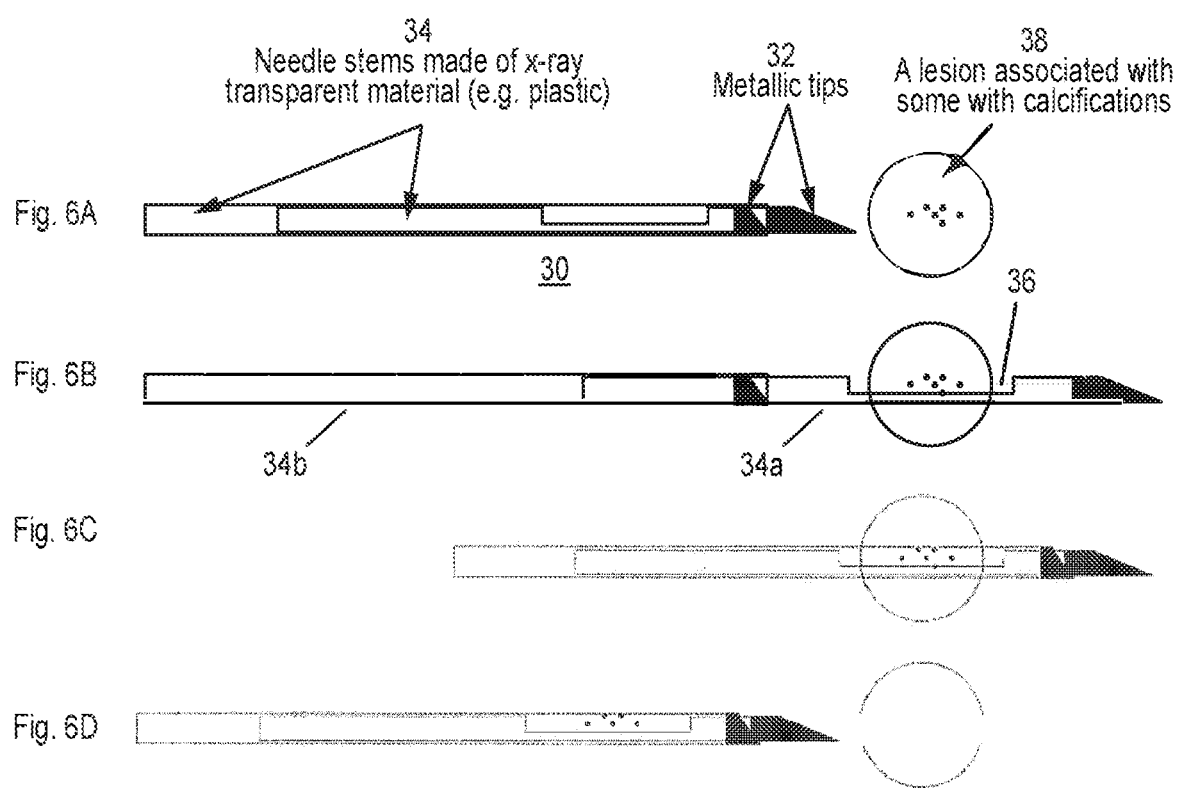

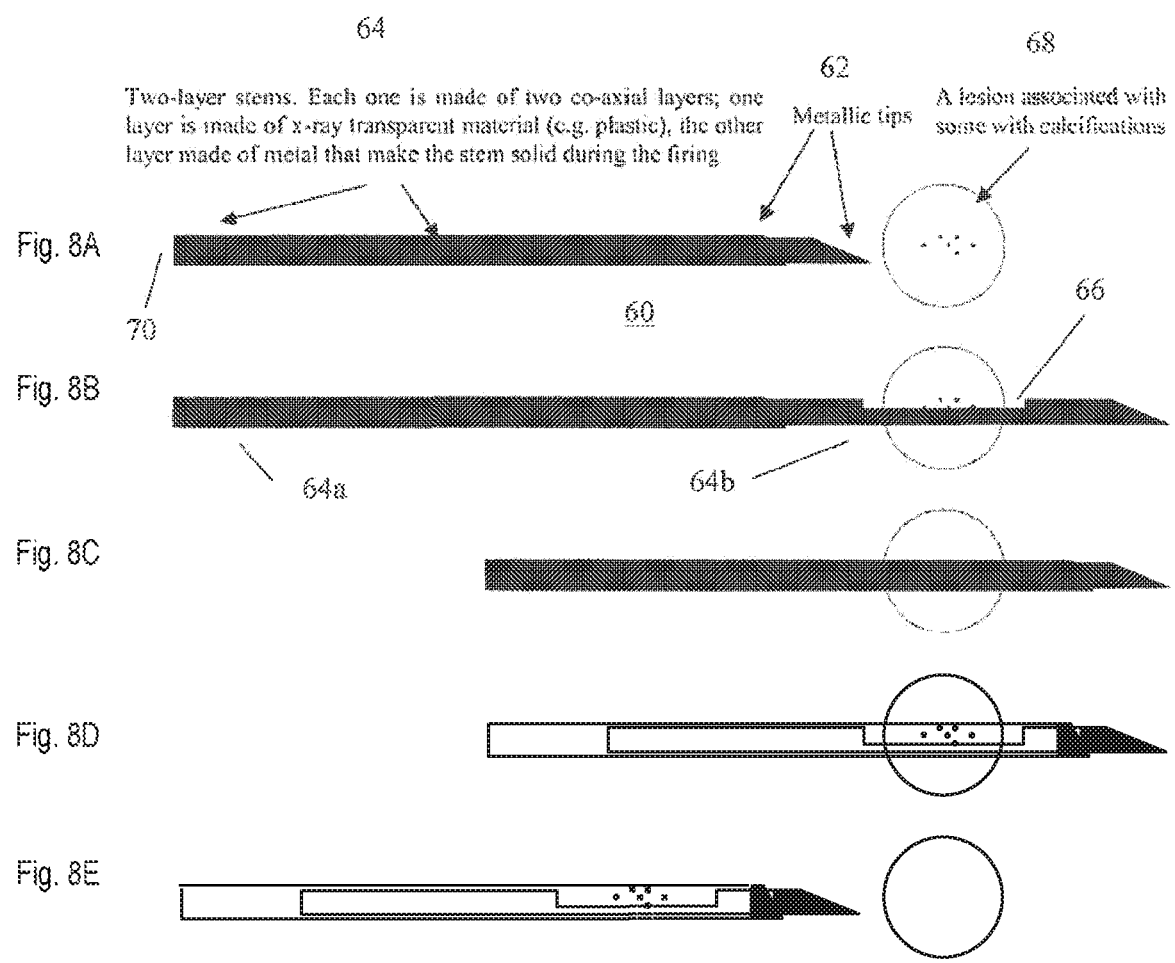

BREAST BIOPSY AND NEEDLE LOCALIZATION USING TOMOSYNTHESIS SYSTEMS

CROSS-REFERENCE TO RELATED APPLICATIONS

This application is a continuation of U.S. patent application Ser. No. 16/936,550, filed Jul. 23, 2020, now U.S. Pat. No. 11,918,389, which is a continuation of U.S. patent application Ser. No. 16/434,064, filed Jun. 6, 2019, now U.S. Pat. No. 11,452,486, which is a continuation of U.S. patent application Ser. No. 15/904,735, filed Feb. 26, 2018, now U.S. Pat. No. 10,335,094, which is a continuation of U.S. patent application Ser. No. 14/021,624, filed Sep. 9, 2013, now U.S. Pat. No. 9,901,309, which is a continuation of U.S. patent application Ser. No. 11/707,587 filed Feb. 15, 2007, now U.S. Pat. No. 8,532,745, which claims Priority from U.S. Provisional Application No. 60/774,142, filed Feb. 15, 2006. To the extent appropriate, a claim for priority is made to each of the above-recited applications.

BACKGROUND AND SUMMARY OF THE DISCLOSURE

Mammography is a well-established method of breast imaging. Using mammograms of the breast, radiologists identify areas suspicious of pathologies. Further identification, such as the determination of cancer is usually done through the taking of a breast biopsy. This is done in several ways. One way is to use mammography to place a wire or needle into the breast, marking the suspected pathology's location. The patient then undergoes an open surgical procedure, and the surgeon can remove tissue from the suspicious area marked by the wire or needle. This is an open surgical biopsy. Another method is known as stereotactic breast biopsy. In this method, using image guidance, a hollow needle is inserted into the breast, and a tissue sample is taken from the area of interest, without a separate surgical procedure. As stated above both methods require some method of localization of the area of interest and a method to direct a wire or needle into the breast so it resides at the already identified area of interest's location.

This patent disclosure covers methods of wire and/or needle guidance into the breast using breast tomosynthesis imaging technology. It covers both upright and prone biopsy equipment.

Tomosynthesis (tomo) is a method of performing three dimensional (3D) breast x-ray imaging. It generates images of cross sectional slices through a compressed breast, and also is used to identify breast pathologies. One of the advantages of tomosynthesis is that the images are three-dimensional, so that once an area of interest is identified in an image, its exact 3D coordinate in the breast can be calculated or estimated, e.g. from the x, y coordinate in the image of a slice and from the z, or depth, coordinate given by the image slice depth location. Another advantage of tomosynthesis is its ability to provide high contrast visibility of objects by the suppression of images from objects at different heights in the breast. Because of its superior contrast visibility, it is expected that there will be pathologies seen on the tomo images that will not be visible using standard x-ray mammography or stereotactic devices or using ultrasound or even MRI or other methods currently employed to provide guidance to the insertion of wires and needles to the location of an identified area of interest. For this reason, it is desired to develop localization methods using tomosynthesis systems that utilize tomosynthesis' natural 3D localization abilities. This patent disclosure addresses both systems and methods for tomosynthesis imaging, and devices and methods for needle and wire localization using tomosynthesis imaging systems. In one non-limiting example, the new approach described in this patent disclosure is based on conventional tomosynthesis designs, e.g. as described in U.S. patent application Ser. No. 10/305,480, filed Nov. 27, 2002, now U.S. Pat. No. 7,123,684, issued Oct. 17, 2006. U.S. patent application Ser. No. 10/723,486, filed Nov. 26, 2003, now U.S. Pat. No. 7,831,296 issued Nov. 9, 2010, U.S. Provisional Patent Application Ser. No. 60/628,516, filed Nov. 15, 2004, International PCT Application Serial No. PCT/US2005/0491941, filed Nov. 15, 2005, published as WO/2006/055830 on May 26, 2006, U.S. Provisional Patent Application Ser. No. 60/631,296, filed Nov. 26, 2004, and International PCT Application Serial No. PCT/US2005/042613, filed Nov. 23, 2005, published as WO/2006/058160 on Jun. 1, 2006, which are hereby incorporated by reference. Typically, the breast is compressed, between a breast platform and a compression paddle. The paddle may be one of the standard paddles used for screening mammography, or one with holes and guide marks used for needle localization or biopsy procedures with conventional mammography equipment, e.g. as described in U.S. Pat. No. 5,078,142 filed Nov. 21, 1989, U.S. Pat. No. 5,240,011 filed Nov. 27, 1991, U.S. Pat. No. 5,415,169 filed Feb. 17, 1993, U.S. Pat. No. 5,735,264 filed Jun. 7, 1995, U.S. Pat. No. 5,803,912 filed Apr. 25, 1995, U.S. Pat. No. 6,022,325 filed Sep. 4, 1998, U.S. Pat. No. 5,289,520 filed Oct. 6, 1992, U.S. Pat. No. 5,426,685 filed Jan. 24, 1994, U.S. Pat. No. 15 5,594,769 filed May 9, 1995, and U.S. Pat. No. 5,609,152 filed Feb. 15, 1995, which are hereby incorporated by reference, and as used in the prone or upright needle biopsy devices commercially available from the Lorad Division of Hologic, Inc. of Bedford, Mass. The x-ray tube is mechanically designed so that it moves along a path that images the breast from differing angles, making a sequence of exposures at differing locations along the path. A digital x-ray image receptor acquires the images. The detector can be stationary during the scan, or it can move during the scan such as if it was mounted on a c-arm connected with the x-ray tube or is otherwise connected to move in sync with the x-ray tube, though not necessarily through the same angle. The entire system can be oriented so that the patient is either upright or lying on a table with her breast pendulant and protruding through a hole in the table and positioned properly on the detector to access the area of interest as needed. One system design would be using a relatively small field of view, such as approximately 5×5 cm. This would correspond to developing a tomosynthesis biopsy system with similar field of view to standard prone table stereo localization systems. However, another way disclosed here, which differentiates a tomo biopsy system from conventional stereo localization system; is to use a significantly larger detector field of view. In one example of an embodiment the field of view can be at least 10×10 cm, in another at least 20×25 cm, in another approximately 24×29 cm.

Localization of an area of interest can start with breast acquisition carried out in a standard way used in breast tomosynthesis. The data is reconstructed, and reviewed. The area of interest is identified either on the reconstructed images of slices, or in the raw projection images. The 3D coordinates of the area of interest can be computed or estimated from the identification of the area of interest on the images.

Once the 3D location of the area of interest is calculated, known methods of directing needles and wires to that location can be used.

There might be some differences in tomo scans during biopsy procedures from screening mammography. The dose might be higher, to get lower noise images. The angular range might be wider or shallower, and the number of projections might be larger or smaller. One might want a wider angle, for example, to get higher precision depth discrimination. One might also want higher resolution for these scans, compared to conventional tomo screening. This could be accomplished through the use of smaller pixel sizes.

A biopsy system used with a tomosynthesis system can include a needle gun assembly with motorized or non-motorized stage that can direct a needle to a specific 3D coordinate in the breast. This stage may be swung or otherwise moved out of the way of the acquisition system during the initial tomosynthesis scan, so that if desired it does not shadow or interfere with the visualization of the breast or breast area of interest.

Following the tomo scan and the identification of the 3D area of interest location, the stage is moved into place. The needle is moved to the 3D coordinate previously identified. The needle may access in the breast via a left or right lateral access (e.g. with the needle roughly parallel to the compression paddle and the patient's chest wall), or it could access the breast with the needle roughly normal to the compression paddle, through an opening in the compression paddle. Or, the needle may enter the breast at an angle between the normal and parallel paths (in relation to the compression paddle and detector) through a hole in the breast compression paddle. It may also come from the front of the breast, directing the needle rearwards towards the chest wall. It can also come from between the paddle and the breast platform but at an angle rather than through the hole in the paddle.

The biopsy system should be capable of working with the tomosynthesis system in all orientations of the tomosynthesis system, including, but not limited to, CC, MLO, and ML and LM imaging orientations. These systems can rotate 360° around the breast and take images from any angle.

Standard techniques of breast biopsy typically involve verification of the needle's location before tissue sampling, known as pre- and post-fire verification. In pre-fire, the needle is inserted into the breast approximately 2 cm short of the center of the area of interest and x-ray exposures are made and images are generated and viewed to verify proper pre-fire needle location relative to the area of interest before tissue sampling. In post-fire, at least one additional exposure is made and the resulting image is viewed to verify proper needle location relative to the area of interest after the firing of the needle and before the tissue is sampled.

These verification images can be images from tomosynthesis scans, or they can be stereo x-ray pairs or individual images. The tomosynthesis scans can be done with different angular ranges and different number of projections and a different dose from conventional tomosynthesis imaging.

Post-fire needle verification can be accomplished in a variety of ways, which may depend on whether the needle access was lateral or tangential. One challenge arises from the fact that the gun and stage and needle are generally radio-opaque and can contribute artifacts to the images if not properly dealt with.

With tangential access, there may be an angular range where the gun and stage shadow the breast. Lateral access may not have the problem of the gun stage in the field of view, but it can have the needle in the field of view, and there might be other mechanics that if imaged can create image artifacts. In general, x-rays from angles that shadow the gun and stage are less useful. Solutions to this problem in accordance with the new approach disclosed in this patent specification include:

a. Development of needle and other sheathing materials that are sufficiently radiolucent that they will not create significant image artifacts. Possible materials are plastics, ceramics, glasses, carbon tubes, and low atomic number metals and other materials. If these materials are used, they can be marked with fiducial markings such as radio-opaque rings or dots allowing visibility in the tomosynthesis images so they can be differentiated from breast tissue or breast area of interest. Alternately, a needle can be used where only the tip (last 1-3 cm) is radiolucent and rest of the needle is radio-opaque.

b. Scanning through angles that do not shadow these objects. This can entail an asymmetric scan geometry, whereby all or an important part of the x-ray beam path does not pass through the needle or other radio-opaque parts. An example is scanning to just one side of the needle.

c. Scanning over a large range, and generally or always avoiding x-ray exposures when the stage or other radio-opaque parts shadow the breast, area of interest or image receptor. Alternatively, x-ray imaging can be done even in angular areas with this shadow problem, but these exposures can be eliminated from viewing or reconstruction, either automatically or through manual elimination via a user interface. Another alternate method involves artifact suppression algorithms used during reconstruction, as in known in tomosynthesis and CT scanning.

d. Stereotactic imaging. Conventional stereotactic imaging involves using a pair of x-ray images at, for example, +15° to the normal to the compression paddle. This geometry involves sufficiently large angles to typically avoid the stage shadows on the image receptor. A tomo system can be used to take tomo projection images at angles that avoid undesirable shadows at relevant parts of the images.

e. Scan angle changes. A larger scan angle than used in conventional tomo imaging can better avoid artifacts from the stage.

f. Bringing the needle to a fixed distance from the lesion. An image can then be taken that does not obscure the area of interest, and the proper distance between needle and area of interest can be verified from imaging. The needle can then be advanced into the correct location within the area of interest based on information from the tomo or conventional imaging while the needle is spaced from the area of interest.

g. In many if not most cases the projection images and perhaps the reconstructed images of breast slices will contain at some location an image of the needle. The needle image can create artifacts in reconstructed images, which can be removed via artifact reduction algorithms as in known in conventional tomosynthesis and CT imaging. One algorithm can involve skipping projection images with extensive shadowing in the projections. Another algorithm can involve segmenting out the needle and other high contrast objects and avoiding reconstruction using these pixels, as has been used in CT and other imaging. Other alternatives include viewing the projection images, which can have images of the needles but no other significant artifacts.

The examples embodiments disclosed in this patent specification can include user interfaces to mark the area of interest location on either the projection tomo images or the reconstructed tomo images of breast slices. Signals directing the needle to the correct location in the breast can be generated automatically based on identifying the location of the area of interest in the images, or the coordinates of the area of interest can be displayed and the needle can be guided to the appropriate location under manual control.

For the pre and post fire images, a facility can be provided to mark the previously identified area of interest location on the current images. This can help visualization of proper needle placement, in case the area of interest becomes harder to see because it has been removed or in case the needle creates large artifacts. The orientation of the needle relative to this mark can provide assurance as to proper location placement.

The 3D nature of the tomosynthesis images allows for calculation of the 3D volume of the area of interest, once it has been identified on the tomosynthesis projections or reconstructed images of slices. This can be part of the display and used to help verify that the correct lesion has been targeted.

BRIEF DESCRIPTION OF THE DRAWINGS

FIGS. 6A-6D, 7A-7E, 8A-8E, 9, and 11 illustrate various biopsy sampling needle designs for reducing undesirable image artifacts.

DETAILED DESCRIPTION OF EXAMPLES OF PREFERRED EMBODIMENTS

Figure 1:
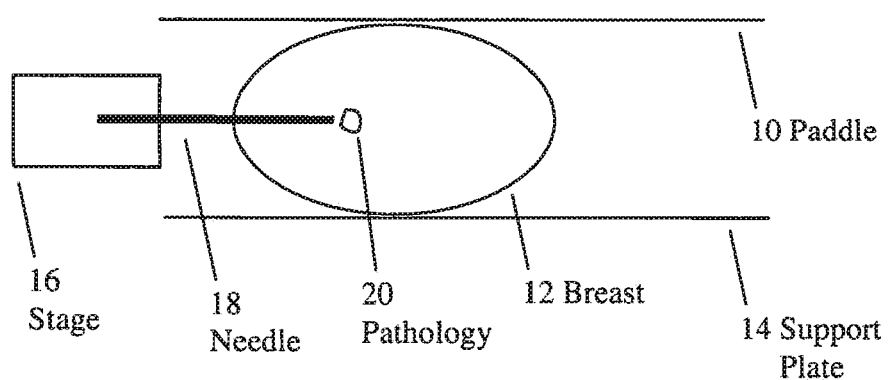
FIGS. 1-5 illustrate various ways of positioning a biopsy needle relative to a breast and imaging positions of an x-ray source and an image plane for reducing undesirable image artifact due to the presence of the needle or other radio-opaque material.

FIG. 1 illustrates lateral needle access, where a breast compression paddle 10 and a breast support plate 14 can be a part of an otherwise known tomosynthesis system such as described in the co-pending patent applications identified above and incorporated by reference in this patent specification, and a biopsy needle stage 16 and a needle 18 such as used, for example, in the patents identified above that pertain to prone biopsy. For clarity, the rest of the tomosynthesis system and other parts of the biopsy apparatus are not shown in this FIG. 1, and a detailed discussion of the basic aspects of tomosynthesis is not included herein. The reader is referred to the references cited herein for such discussions. For example, image reconstruction can be performed using filtered back projection (for rapid speed of reconstruction) and/or artifact reduction methods (such as ordered statistics backprojection), as disclosed, for example, in U.S. Patent Application Publication No. 2002/0113681, the entire contents of which are incorporated by reference herein.

A patient's breast 12 is compressed between paddle 10 and support plate 14 and a needle biopsy stage 16 has been used to position the tip of a biopsy needle 18 near an area of interest 20 in breast 12. In this example needle 18 enters the breast 12 generally laterally, i.e. along the plane of support plate 14 and along the chest wall of the patient, and from the left as seen in the drawing. Of course, the needle 18 can enter instead from the right, and need not be exactly parallel to support plate 14 or to the chest wall, but can be at any angle thereto that the health professional doing the needle biopsy finds suitable for the particular patient or area of interest location. As described above, the location of area of interest 20 has been determined based on tomosynthesis images that can be tomo projection images and/or tomo reconstructed slice images. In FIG. 1, the patient's chest is behind the illustrated structure and is generally along the plane of the sheet. If upright biopsy is used, the patient's chest wall would be generally vertical; if a prone biopsy table is used, the patient's chest wall would be generally horizontal.

Figure 2:
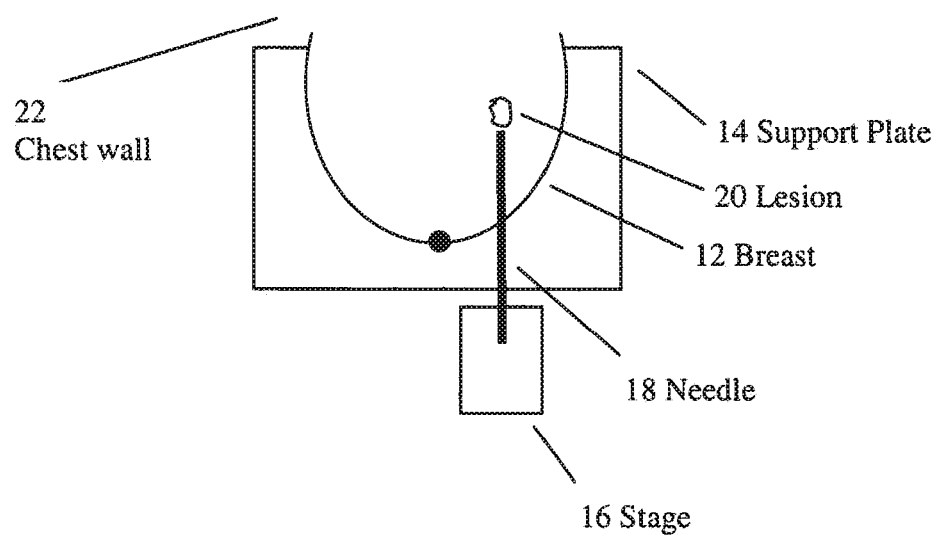

FIG. 2 illustrates frontal needle access in which needle 18 accesses area of interest 20 from the front of breast 12, in a direction generally along the plane of support plate 14 and normal to chest wall 22 of the patient. Again, the needle 18 direction need not be exactly parallel to support plate 14 or normal to chest wall 22, but can be at any convenient angle thereto that would allow the tip of needle 18 to reach area of interest 20 generally from the front of the breast 12, at either side of the nipple. In FIG. 2 the patient's chest wall 22 is generally normal to the sheet.

Figure 3:
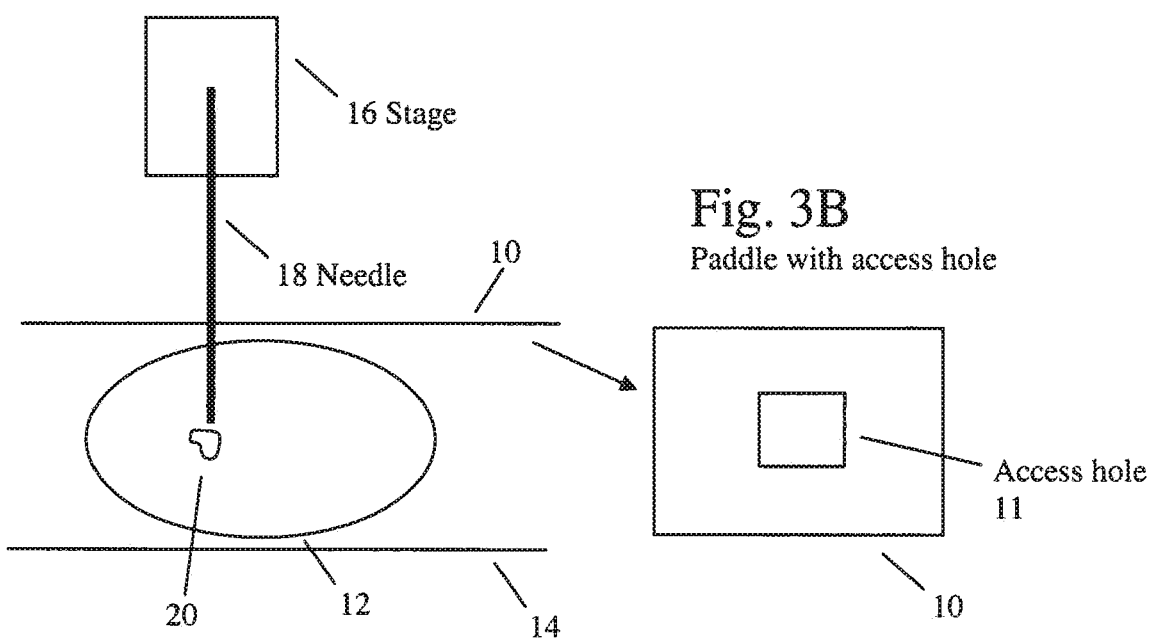

FIG. 3a illustrates tangential needle access, where a breast compression paddle 10 has, as seen in FIG. 3b, one or more needle access holes 11. FIG. 3a illustrates breast compression paddle 10, breast 12 and support plate 14 in a view similar to that of FIG. 1, but a needle stage 16 and needle 18 at a position above the breast. Needle 18 accesses area of interest 20 in a direction generally normal to support plate 14 and along the chest wall (not shown) of the patient. Again, needle 18 need not be at the angles shown but may be at any angle that the health professional doing the biopsy finds suitable.

Figure 4:
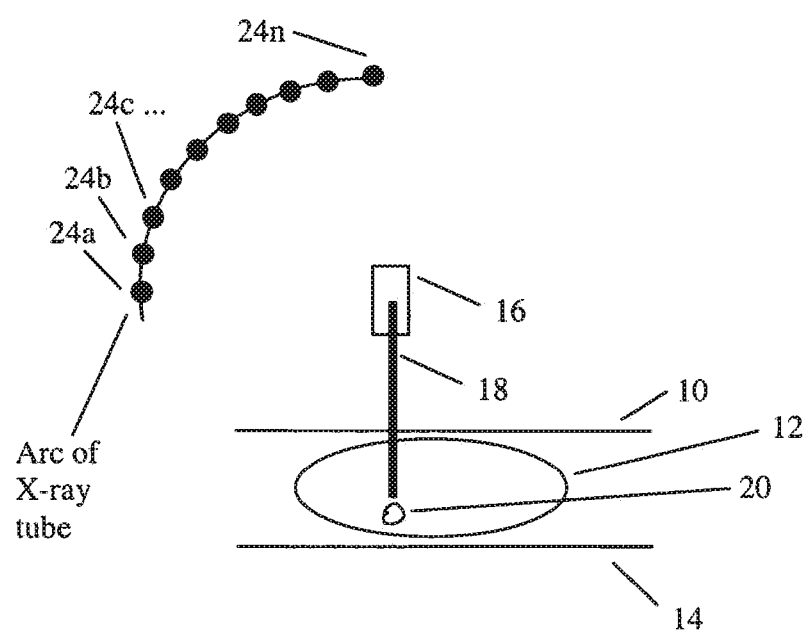

FIG. 4 illustrates one type of a tomo scan that can be used to reduce undesirable image artifacts due to the presence of a biopsy needle 18 and possibly other radio-opaque materials. While FIG. 4 illustrates tangential needle access similar to that of FIG. 3, the principles discussed below in connection with FIGS. 4 and 5 apply to any other type of access to area of interest 20. FIG. 4 illustrates positions 24a, 24b, . . . , 24n of an x-ray tube (not shown) from which the tube emits x-ray beams for taking tomo projection images. While positions 24a-24n are illustrated as being along an arcuate path, they can be along a differently shaped path, and scanning can start from either end of the path, or from an intermediate positions along the path. As evident from FIG. 4, it is likely that at some positions of the scan, needle stage 16 would obscure at least a significant part of the imaging x-ray beam and the resulting projection image is likely to have significant and probably unacceptable artifacts.

Figure 5:
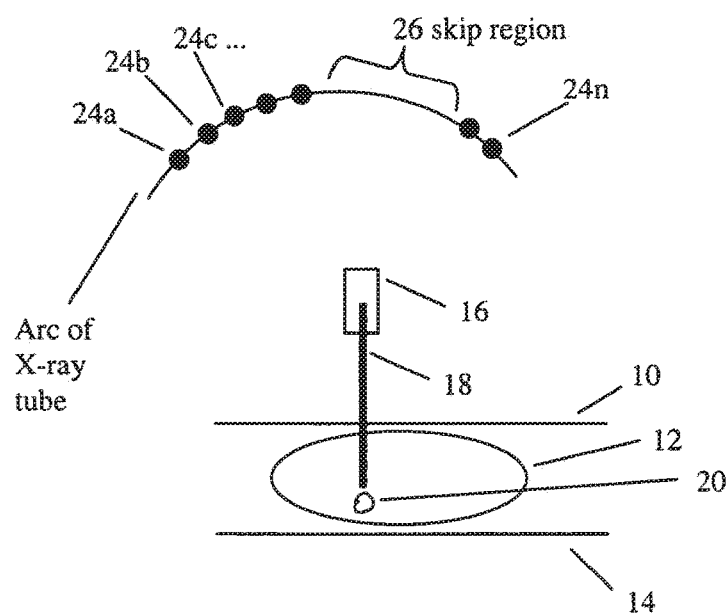

FIG. 5 is otherwise similar to FIG. 4 but illustrates a gap region 26 in the path of x-ray tube positions 24a-24n. No x-ray tomo exposures are taken from positions in this gap region 26. Exposures are taken from positions outside this region to minimize or at least significantly reduce the extent to which the needle stage 16 and any other x-ray opaque materials affect the imaging x-ray beams and thus reduce undesirable artifacts in the images relative to images that could have been obtained with exposures taken from positions in gap 26. Sufficient tomo projection images can be taken from positions outside gap 26 from which acceptable tomo reconstructed images of breast slices can be computed to localize needle 18 relative to area of interest 20. Gap 26 can be at an end of the path of positions 24a-24n or it can be intermediate positions 24a-24n. Different x-ray dose can be used for different ones of positions 24a-24n, e.g. less dose for exposure positions in which radio-opaque materials in the path of the x-ray beam are likely to generate more undesirable artifacts, and greater dose for positions in which such material are less likely to produce such artifacts. It is possible to take exposures even from positions in gap 26, preferably at low x-ray dose, but not use the resulting projection images for reconstructing tomo images of breast slices.

During the x-ray tomo exposure, metallic breast biopsy needles can obstruct the sampled lesion or cause other undesirable artifacts such as, for example, streaking artifacts in reconstructed tomosynthesis images. This is especially acute where the sampled lesions are calcifications. This obstruction can reduce the accuracy of biopsy. Embodiments of the present disclosure include a needle design that allows for better visibility of the sampled lesion.

Several embodiments of such needles are shown m FIGS. 6-8. Here, x-ray transparent material is used in the construction of the stem of the needle to a significant extent so the sampled lesions can be seen more clearly when imaged with tomosynthesis or 2D mammography. The needle stem should still be solid enough to cut the tissue and the lesion. Of course, the x-ray transparent material need not be perfectly transparent but only sufficiently transparent to minimize or at least significantly reduce undesired image artifacts as compared with the use of metallic needles without such material. The term "x-ray transparent" is used in this sense in this patent disclosure.

FIGS. 6A-6D illustrates the use of a breast biopsy needle with an x-ray transparent body according to embodiments of the present disclosure. The needle 30 consists of two metallic tips 32 for cutting the tissue and lesion 38, and two needle stems 34 made of x-ray transparent material so as not to block x-rays. Because the needle stems 34 are x-ray transparent, the position of the needles may be determined by the position of the needle tips 32 in x-ray images and the known needle geometry. FIG. 6A illustrates the needle 30 prior to its firing. The relative location of the needle and the lesion 38 are confirmed using x-ray tomosynthesis (or 2D x-ray mammography).

FIG. 6B illustrates that one of the two needle stems 34 may have a notch 36. The notched needle stem 34a may be within the lumen or cannula of the un-notched needle stem 34b. The notched needle stem 34a may be fired from the un-notched needle stem 34b such that the notch is placed in proximity to the lesion 38. FIG. 6C illustrates that the un-notched stem 34b may be pushed to close around the notched stem 34a thereby cutting and trapping the lesion 38, or at least a part thereof, within the notch 36 and the cannula of the un-notched stem 34b. Tomosynthesis or 2D mammography may then be used to confirm the position of the lesion 38 within the notch 36 and the cannula of the un-notched stem 34b. FIG. 6D illustrates that the needle may be removed from the patient with the trapped lesion 38. Tomosynthesis or 2D mammography may then be used to confirm that the lesion 38 has been correctly sampled.

Figure 7A:
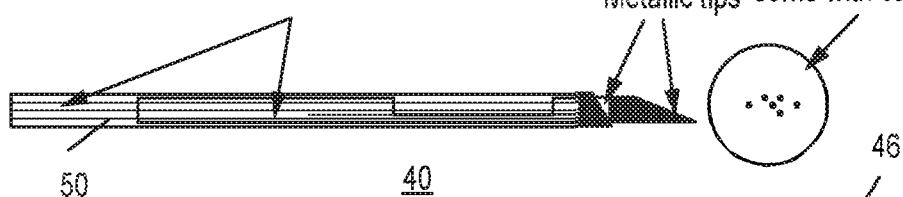
Figure 7B:
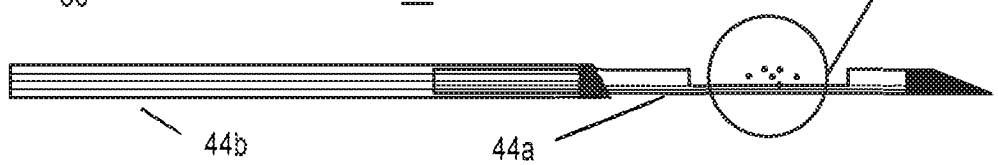
Figure 7C:
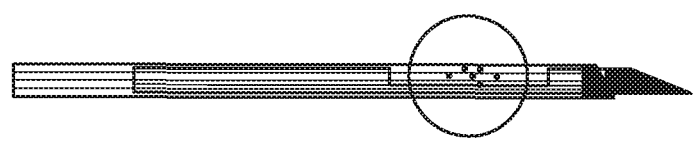
Figure 7D:
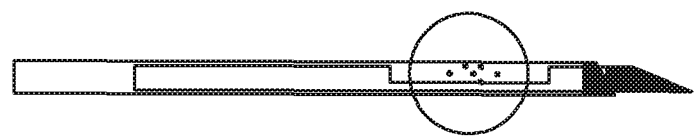
Figure 7E:
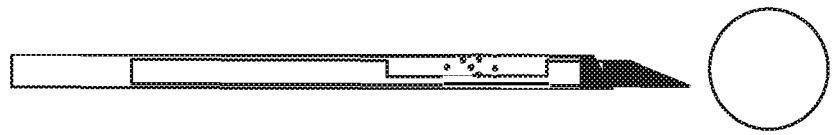

FIGS. 7A-7E illustrate the use of a breast biopsy needle with an x-ray transparent body stiffened with metal according to another embodiment of the present disclosure. The needle 40 comprises two metallic tips 42 (to cut the tissue and lesion 48), and two needle stems 44 made of x-ray transparent material (so as not to block or scatter x-rays excessively) and removable solid metallic wires or ribs 50 to enhance the structural integrity of the needle stems during the firing. The wires or ribs 50 can be removed from the stems, after firing, to allow the needle stems 44 to be x-ray transparent and the taking of x-ray images after the wires or ribs 50 have been withdrawn. As seen in FIG. 7A, before firing the needle 40, the relative location of the needle 40 and the lesion 48 may be confirmed using tomosynthesis or 2D mammography. As seen in FIG. 7B, a notched needle stem 44a may be fired from an un-notched needle stem 44b. As seen in FIG. 7C, the un-notched needle stem 44b may be pushed to the notched needle stem 44a so as to cut and trap the lesion 48 between the notch 46 of the notched needle stem 44a and the un-notched needle stem 44b. As seen in FIG. 7D, the metallic wires 50 can be removed from the needle stems 44 prior to performing tomosynthesis or 2D mammography to confirm the location of the lesion 48. As seen in FIG. 7E, the needle 40 may be removed from the patient with the trapped lesion 48. Tomosynthesis or 2D mammography may then be used to confirm that the lesion 48 has been correctly sampled.

FIGS. 8A-8E illustrate another embodiment of a new breast biopsy needle that comprises two coaxial bodies each having an x-ray transparent (e.g. plastic) layer and an x-ray opaque (e.g. metal) layer that adds mechanical strength or stiffness but can be withdrawn, if desired, after the needle is in place in the breast but before x-ray images are taken. As seen in FIG. 8A, needle 60 is inserted into the breast until its cutting tips 62 are close to but spaced from suspected lesion 68. At this time, the relative locations of the needle and the lesion can be confirmed by taking tomosynthesis or 2d mammography images. Then, as seen in FIG. 8B, the notched stylet 64b (the notch shown as 66) of the needle can be fired into lesion 68 to sample it and, as seen in FIG. 8C the cannula 64a can be pushed in to slice the lesion or at least a part of it into the notch. Then the radio-opaque metal layers can be withdrawn from each of the cannula and the stylet to leave the x-ray transparent structure seen in FIG. 8D (except for its cutting tips 62). At this time, post-fire tomosynthesis or 2D mammography images can be taken to confirm that the lesion or a part of it is in the notch. Because of the use of x-my transparent material at the lesion at this time, the post-fire images are unlikely to suffer from undesirable artifacts. The core system can then be pulled back with the lesion sample, e.g. to the position illustrated in FIG. 8E.

Figure 9:
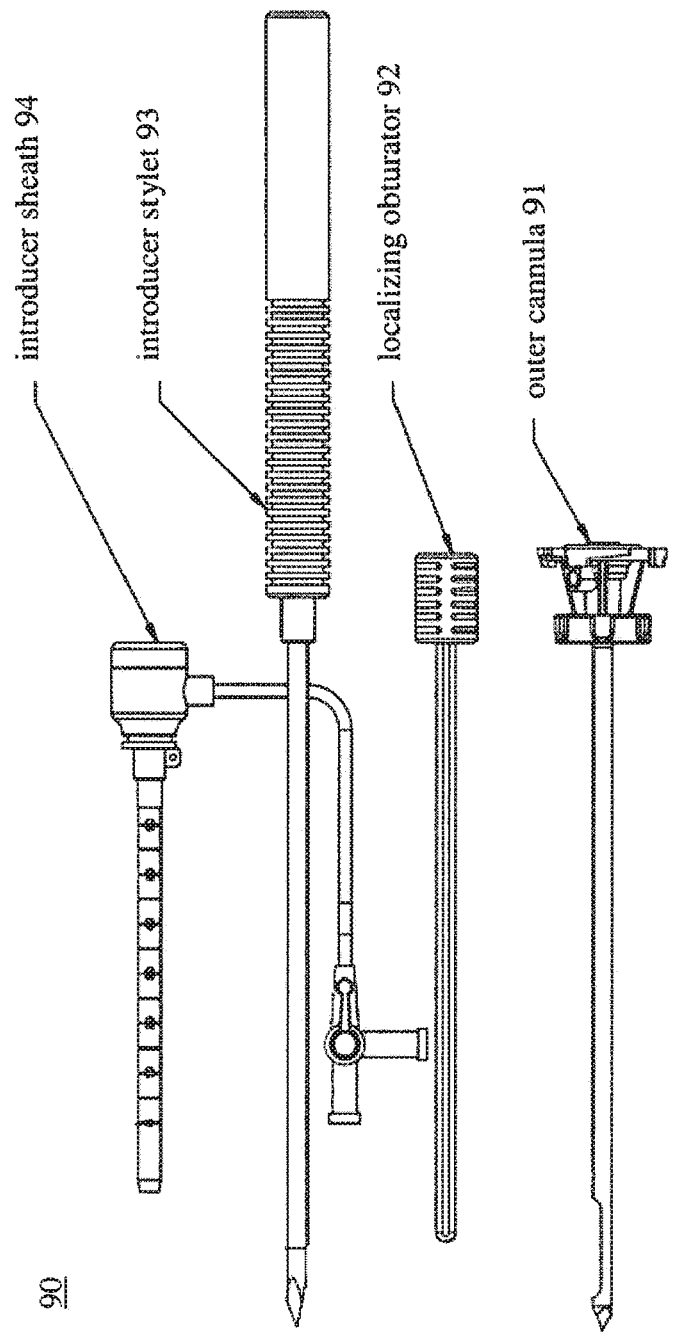

FIG. 9 illustrate another example of a new breast biopsy needle. Biopsy needle 90 is configured as "tube-within-a-tube" cutting device and includes an outer cannula 91, an inner cannula (or localizing obturator) 92, an introducer stylet 93 and an introducer sheath 94. In addition, the outer cannula 91, localizing obturator 92, introducer stylet 93 and introducer sheath 94 can be mounted to a handpiece (not shown) or an attachment (not shown) which is in turn coupled to a support fixture or positioning device for moving the biopsy needle to a desired position. The outer cannula 91 defines an outer lumen and terminates in a tip which is preferably a trocar tip that can be used to penetrate the patient's skin. The localizing obturator 92 fits concentrically within the outer cannula 91. The localizing obturator 92 can be driven by a rotary motor and a reciprocating motor drive to translate the localizing obturator 92 axially within the outer cannula 91, while rotating the localizing obturator 92 about its longitudinal axis (or the localizing obturator 92 can be rotated and/or translated manually). Alternatively, the introducer stylet 93 which is inserted in the annular introducer sheath 94 can be inserted. In this example, the introducer stylet 93 and/or sheath 94 can be radiolucent with a radio-opaque band at a distal end thereof.

Additional examples of breast biopsy needles are disclosed in U.S. Pat. Nos. 6,638,235, 6,758,824, 6,620,111 and 6,626,849 and U.S. Publications Nos. 2006/0155209 A1, 2006/0129062 A1, 2006/0030784 A1, 2005/0113715 A1, 2005/0049521 A1, and 2004/0267157 A1, the entire contents of which are incorporated herein by reference.

Thus, in one aspect this patent specification discloses a method and a system in which tomosynthesis reconstructed images of slices of a patient's breast and/or tomosynthesis projection images of the breast are used to (1) identify the location of a suspected area of interest in the breast, (2) guide needle biopsy of the area of interest, (3) confirm pre-fire position of the needle relative to the area of interest, and/or (4) confirm post-fire position of the needle relative to the area of interest. One unique benefit of this approach is with respect to suspected pathologies that can be seen or assessed better in tomosynthesis images than in conventional mammograms or in conventional ultrasound images of breast tissue. The method and system involve taking a series of tomosynthesis projection images at respective different angles of the imaging x-ray beam relative to the breast, for example in the manner disclosed in said patent applications that are incorporated by reference in this patent specification. The information from these projection images is reconstructed into images of slices through the breast, which may represent slices of selected thickness and selected angles relative to the breast platform or the imaging plane(s) of the projection images. Typically but not necessarily the reconstructed images represent slices that are parallel to the breast platform and thus to the plane of a conventional mammogram. These images are used to identify the location of the area of interest in the breast in three dimensions, for example by having the health professional point to the location of the area of interest in one or more images and using the system to compute the 3D coordinates of the location in a manner similar to that used in said biopsy system patents identified above and incorporated by reference in this patent specification, or in a different manner, such as by pointing to the area of interest in a reconstructed slice image to thereby identify the location of the area of interest in two dimensions in the plane of the slice and to provide the third dimension from knowledge of the depth of the slice in the breast. This 3D information of the area of interest location can be used together with information regarding a geometrical relationship between the equipment in which the breast of compressed and immobilized to determine the direction and extent of biopsy needle motion executed by a needle stage in a manner similar to that disclosed in said patents incorporated by reference herein, to position the needle, to sample the area of interest and to confirm pre-fire and post-fire locations of the needle relative to the area of interest.

In order to reduce undesirable artifacts in the x-ray images due to the presence of radio-opaque objects such as the biopsy needle in the imaging x-ray beam, the method and system disclosed here employ new approaches either singly or in combinations or subcombinations with each other. A first new approach in this respect pertains to selection of tomosynthesis images and involves taking projection tomosynthesis images only at angles in which the radio-opaque objects are not in the imaging x-ray beam or, if they are in the beam, their effect in the image is significantly less than it would have been for other possible beam angles. This may involve not taking projection images at angles that would produce more undesirable artifacts and/or taking such projection images but not using them in reconstructing slice images. A second new approach that can be used instead of or in addition to the first one is to carry out post-processing of the tomo images to reduce artifact therein due to the presence of radio-opaque objects in the beam. This can involve processing of the reconstructed slice image, e.g. by using streak artifact removal algorithms similar to those conventionally used in CT (computerized tomography) technology, and/or image processing of the tomo projection images to remove or reduce such artifacts. A third new approach that can be used instead of one or more of the first and second, or together with one or both of the first and second, is to use biopsy equipment that reduces or avoids such image artifacts, e.g. a biopsy needle that is made at least partly of a material that is significantly more x-ray transparent than conventional biopsy needles. A needle made of such material can be used as is for insertion into the breast and for tissue sampling, or it may be stiffened by portions of an x-ray opaque material such as metal that are used for insertion and/or tissue sampling but are withdrawn from the breast or at least from the immediate vicinity of the area of interest before pre-fire and/or post-fire x-ray images can be taken to thereby avoid the image artifacts that such metal would cause if not withdrawn. As one example, such stiffening portions can be in the form of pins or ribs inside a cannula. As another example, they can be sleeves coaxial with a cannula and/or a stylet. Other examples of stiffening portions that are withdrawn before pre-fire and/or post fire imaging also are contemplated.

Figure 10:
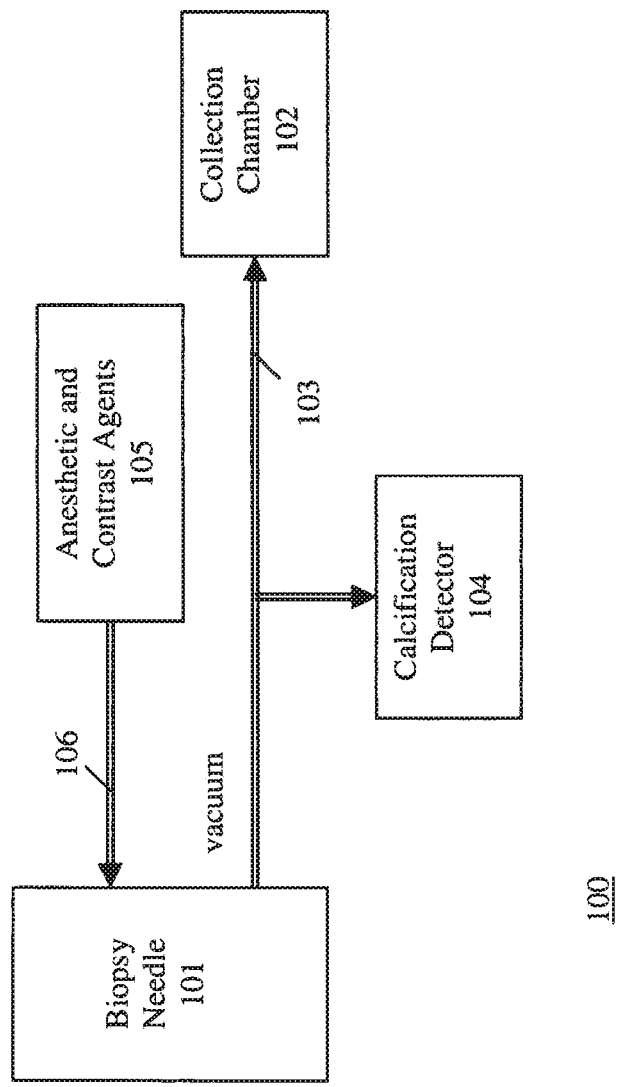
FIG. 10 shows a block diagram of a system with additional optional features.

Additional features can be added. For example, in the system 100 shown in FIG. 10, a calcification detector 104 is added in a sample delivery path 103 between a biopsy needle 101 and a collection chamber (or filter) 102. The sample delivery path 103 typically includes a tube or other channel for delivery of the extracted sample to the collection filter 102. The calcification detector 104 can be coupled to the sample delivery path 103 to determine whether the samples include calcifications and estimate an amount of the calcifications. The calcification detector 104 can include, as an example, an x-ray source and detector for imaging the samples passing through the sample delivery path 103, and a CAD (computer aided diagnosis) component configured to detect and count the number of calcifications in the samples.

Figure 11:
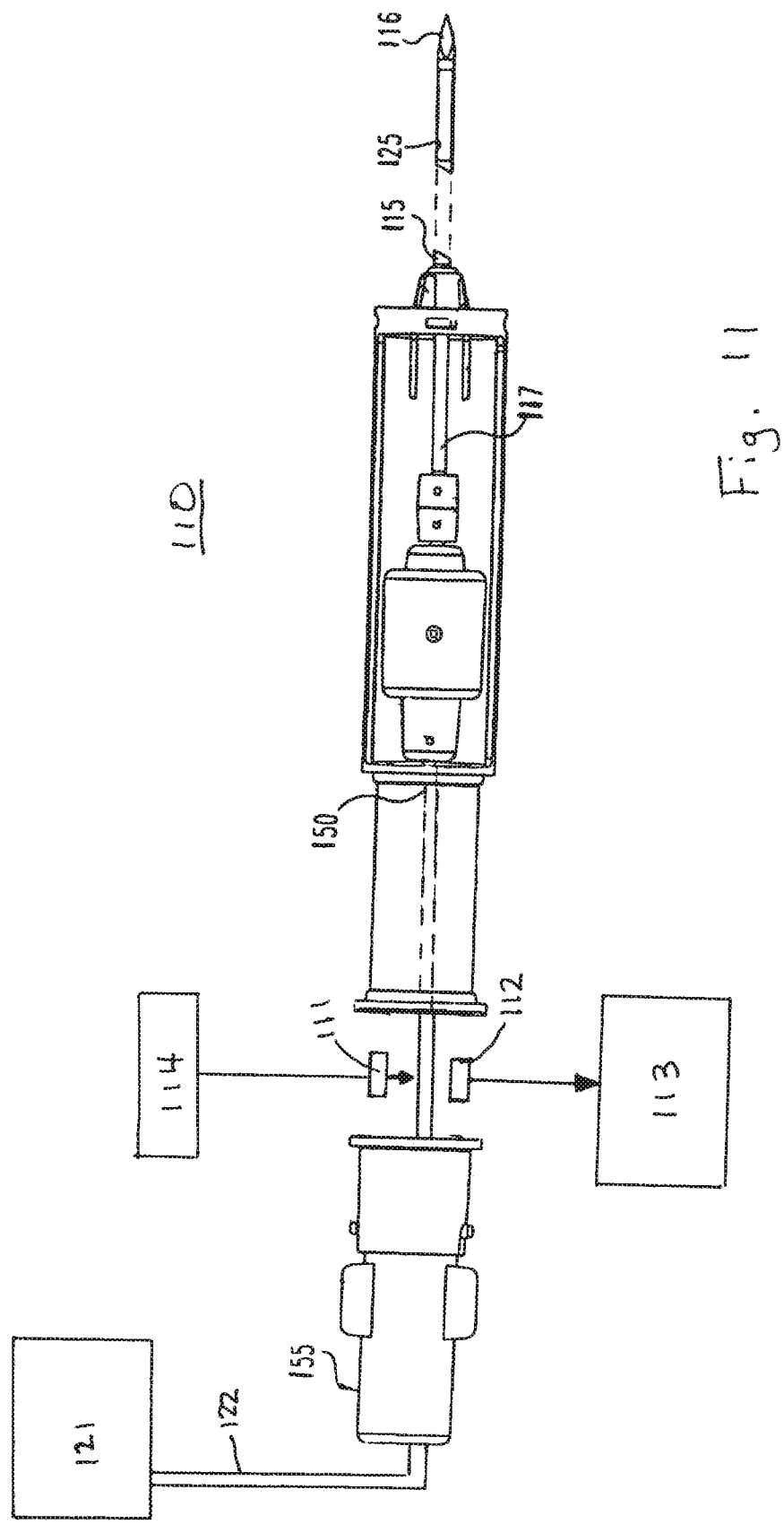

In one example (FIG. 11), a tissue biopsy apparatus 110 configured as a handheld device (although the apparatus can also be mounted to a support fixture that is used to position the biopsy needle) includes a biopsy needle mounted to a handpiece. The biopsy needle includes an outer cannula 115 terminating in a tip 116. A tissue-receiving opening 125 is provided (relatively) near the tip 116. An inner cannula 117 fits concentrically within the outer lumen of the outer cannula 115. The inner cannula 117 is rotated (for example, by a rotary motor) about its longitudinal axis and is translated axially within the outer cannula 115 (for example, by a reciprocating motor drive). The outer cannula 115 terminating, tip 116, inner cannula 117 and tissue-receiving opening 125 interoperate similar to the other examples discussed above to extract biopsy samples of a patient's breast. The inner cannula 117 provides an avenue for aspiration of the biopsy samples to the tissue aspiration path which also includes aspiration tube 150 coupling the tissue aspiration path to a collection chamber 155. Aspirator 121 applied vacuum or aspiration pressure to the collection chamber to draw samples through the tissue aspiration path to the collection chamber 155. X-ray tube 111 and detector 112 operate under appropriate control of a controller 114, and a detection signal representing the x-rays received by the detector 112 from the source 111 is output to CAD component 113 which decodes the signal to determine whether the samples include calcifications and estimates an amount of the calcifications. CAD systems and techniques are well-known in the art, and therefore a detailed discussion of such systems and techniques is omitted from this disclosure in the interest of clarity and brevity.

In the case that the collection filter is integrated with the biopsy needle in a handheld device or in a needle stage, the x-ray tube and detector would be small-scaled. An example of a small scale detector is available from Hamamatsu, Corporation, Bridgewater, New Jersey (see http://sales.hamamatsu.com/en/products/electron-tube-division/x-ray-products/x-ray-flat-panel-sensor.php). Information regarding a small scale x-ray tube (40 kV metal-ceramic X-ray tube from Newton Scientific Inc., Cambridge, Massachusetts) is available at http://www.newtonscientificinc.com/swans.htm.

Figure 12:
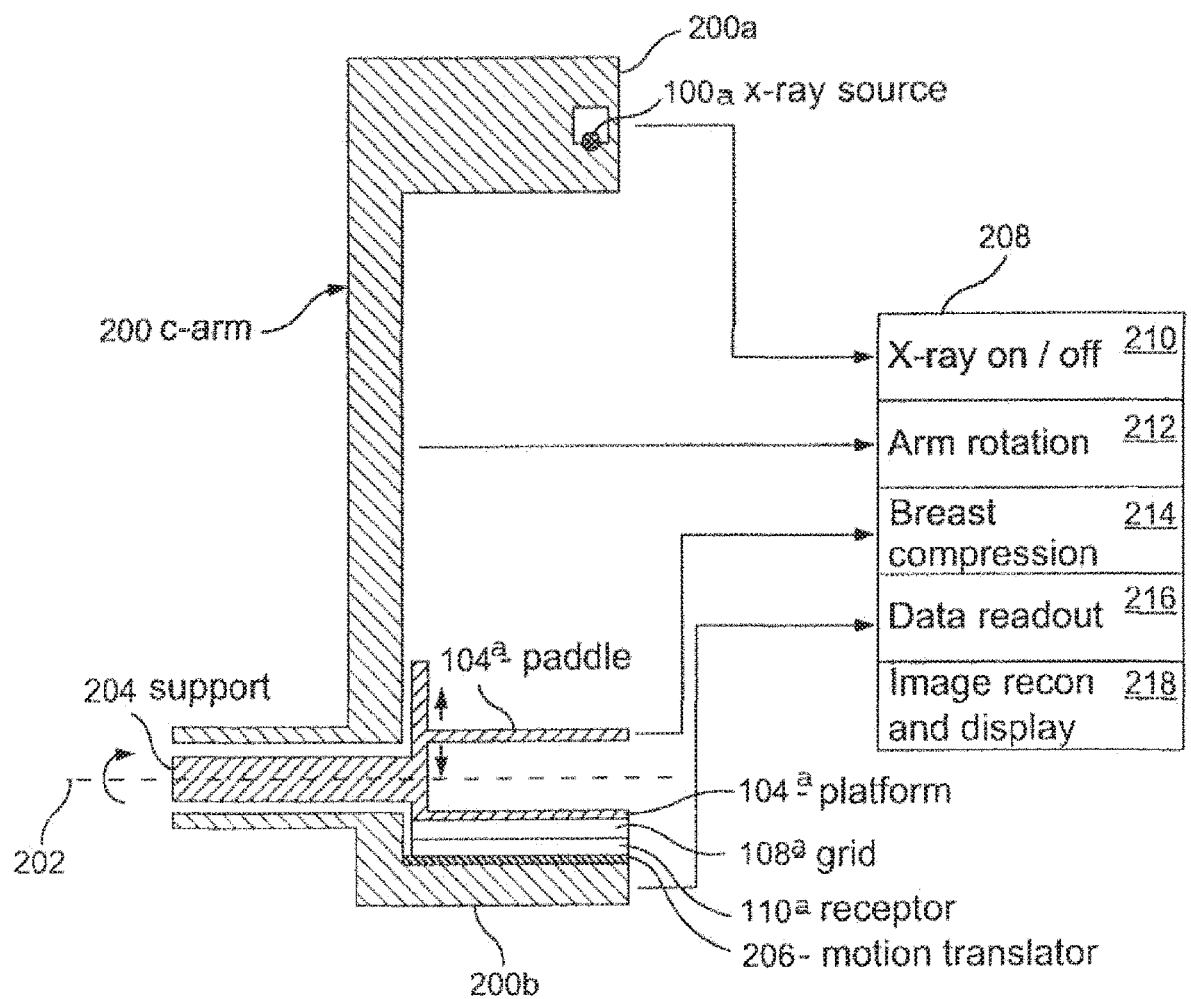
FIGS. 12-14 illustrate a tomosynthesis system and its operation.

FIG. 12 schematically illustrates a side view of a system comprising x-ray source 100a at one end 200a of a C-arm 200 that is supported for selective rotation about an axis 202, independently of a support 204 for compression paddle 104a and breast platform 106a. Support 204 also selectively rotates about the same axis 202. The other end 200b of C-arm 200 interacts with x-ray receptor 110a through a motion translator schematically illustrated at 206 that translates the rotational motion of the end 200b about axis 202 to a substantially translational motion of receptor 110a that substantially maintains the distance of receptor 110a from breast platform 106a while x-ray data is being taken. FIG. 2 is not to scale, and receptor 110a can be spaced further from member 200b than illustrated, to allow more space for motion translator 206, and also to allow for receptor 110a to be moved selectively further from or closer to breast platform 104a and thus allow for x-ray image magnification. In operation, C-arm 200 and support 204 are rotated to desired angular positions, either manually or by motor drives, patient breast 102a is positioned on platform 106a and is immobilized by bringing paddle 104a toward platform 106a and compressing breast 102a, with typically the same or less force than for a typical conventional mammogram, such as between one to one-third the conventional force. With breast 102a immobilized, and with C-arm at a selected angle relative to a normal to platform 106a and receptor 110a, such as +15°, imaging starts, and a projection image is taken for each of a number of selected angular positions of source 100a while C-arm 200 rotates, continuously or intermittently, through a selected angle, such as an angle of 30°, i.e. from +15° to −15°. Of course, the motion can be in the opposite direction, from −15° to +15°, or can be over a different angular interval, such as over less than a total of 30°, e.g. 25°, 20°, etc., or more than 30°, such as 35°, 40°, etc. Currently, the preferred range is +15°. A set of image data can be taken at selected angular positions, such as every degree, or every fraction of a degree; or every several degrees of angle. The angular increments between the different positions for sets of image data need not be the same. For example, the increments around 0° can be less than those at the extremes of the angular positions, or vice versa. Currently, the preferred angular increment is 3°. The sets of image data can be taken after an incremental motion from one angular position of source 100a to another, and from one translational position of receptor 110a to another, such that source 100a and receptor 110a are stationary white a set of image data is being taken. Alternatively, one or both of source 100a and receptor 110a can move continuously while sets of image data are being taken, one set for each increment of continuous motion. In the currently preferred embodiment, in the example of continuous motion while taking image data both source 100a and receptor 110a move while image data are being taken.

FIG. 12 also illustrates schematically an electrical/electronic system 208 that interacts with the components discussed above. System 208 includes a control 210 for selectively energizing and otherwise controlling x-ray source 100a, an arm rotation control 212 for selectively rotating C-arm 200 and support 204, a breast compression control 214 for selectively moving compression paddle 104a toward and away from breast platform 106a, data readout electronics 216 coupled with x-ray receptor 110a to read out the sets of image data at the respective positions of source 100a and receptor 110a relative to immobilized breast 102a, and an image reconstruction and display unit 218 coupled with data readout electronics 216 to receive the sets of image data from electronics 216 and to process the image data for reconstruction and other purposes and display images.

For a given position of breast 102a, such as a position that is the same or similar to the CC position for a conventional mammogram, source 100a and receptor 110a can be positioned relative to immobilized breast 102a such that at the 0° position a center ray of the x-ray beam from source 100a would be substantially normal to receptor breast platform 106a and receptor 110a. For a first set of image data, source 100a is at + (or −) 15° in a preferred example, and is gradually moved; continuously or intermittently to −(or +) 15°, with a set of image data taken every 3°. The angular range and the increment over which data sets are taken can each be selectively set by the operator, depending of characteristics of the breast being imaged and the screening and diagnostic needs, and can be different for different patients or from one to the other breast of the same patient. For example the source can move through angles that range from a fraction to a degree to several degrees from one imaging position to the next. Each set of image data is supplied by image readout 216 for processing at image reconstruction and display unit 218. Each set of image data can be taken at the same x-ray dose to the breast, and the dose at any one of the different imaging positions can be substantially less than that for a conventional mammogram. The x-ray dose can be substantially the same for each imaging position, but preferably the dose at one of the position, e.g., at or close to the 0° position, is the same or similar to dose for a conventional mammogram while the dose at the each of the other positions is less, preferably much less. Alternatively, the scan can begin with or end with an exposure close to the 0° position at a dose similar to a conventional mammogram, and the rest of the set of image data can be over the angular range with each exposure at an x-ray dose that is substantially less than that for a conventional mammogram. Thus, two types of images can be produced in accordance with the currently preferred embodiment while breast 102a is immobilized in the same position. One type is the same or is at least similar to a conventional mammogram, which can be read and interpreted in the manner familiar to health professionals. The other type is tomosynthetic images reconstructed from the image data and displayed either separately or as an adjunct to the display of the image that is the same or similar to a conventional mammogram. The process described above for one position of breast 102a can be repeated for another position. For example one process can be for a breast position in a manner that is the same or similar to positioning the breast for a conventional CC view, the breast can then be released, the support 204 and C-arm 200 rotated to other angular positions and the breast repositioned in a manner that is the same and similar to the position for an MLO view, and the procedure repeated.

Figure 14:
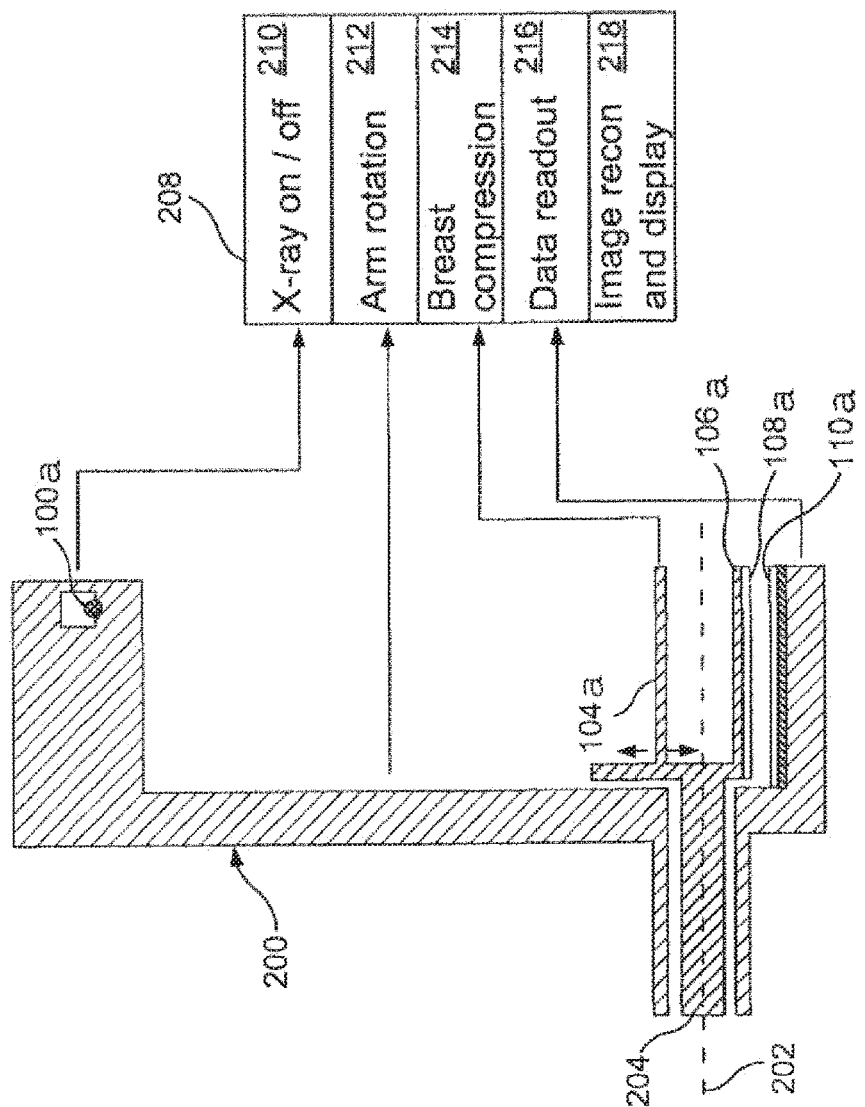
Figure 13:
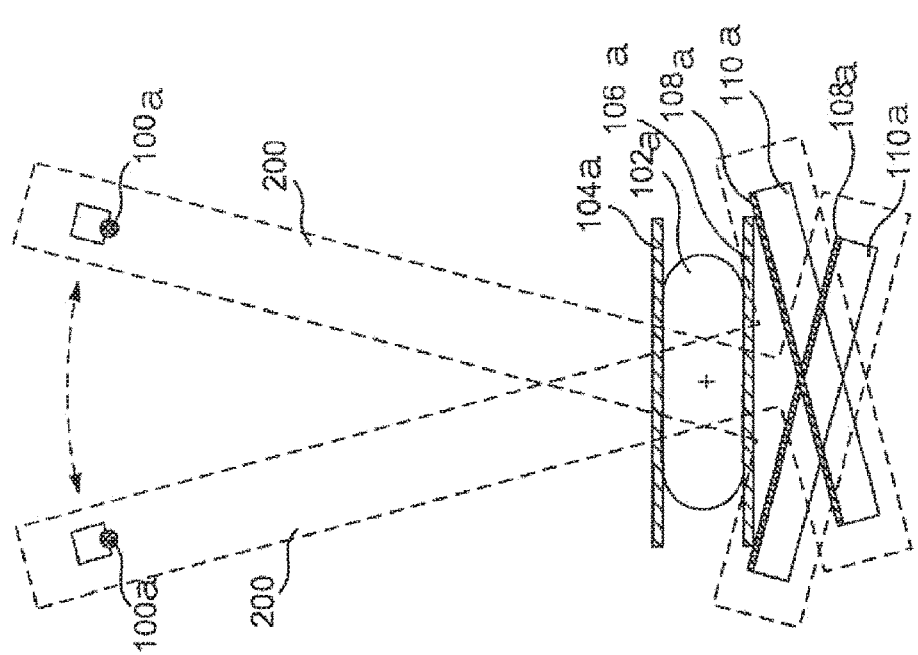

An alternative embodiment, illustrated schematically in a front view in FIG. 13 and in side view in FIG. 14, is similar except that receptor 110a is affixed to the end 200b of C-arm 200 that is opposite x-ray source 100a. In this embodiment, receptor 110a moves relative to immobilized breast 102a along an arcuate path from one imaging position to another. Because the change in angle between receptor 110a and breast platform is small, it can be disregarded in processing the sets of x-ray image data. Alternatively, a geometric correction known to those skilled in the art can be applied to each set of image data to convert it to interpolated pixel values that would correspond to those that would have been obtained if receptor 110a had been parallel to and at the same distance from platform 106a at all imaging positions. The so corrected sets of image data can then be used in filtered back projections as described above.

Figure 15:
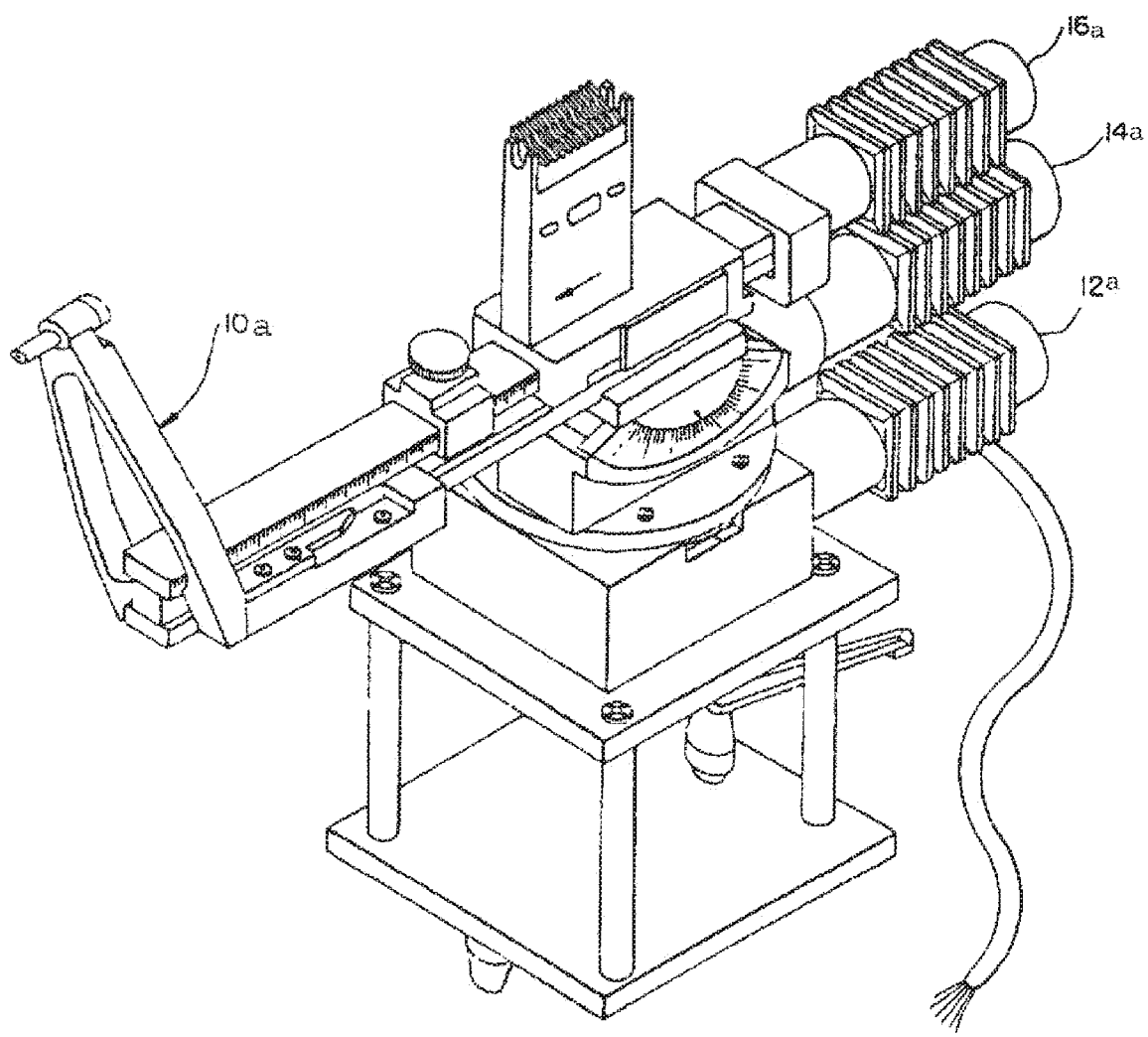
FIGS. 15-18 illustrate a biopsy stage and its operation.

FIG. 15 illustrates a biopsy needle positioning mechanism that is typically employed as a component of an overall mammographic needle biopsy system, and comprises a conventional puncture instrument 10a for retaining a biopsy needle or other biopsy or therapeutic delivery device (not illustrated). Three conventional DC motors 12a, 14a, and 16a are provided for moving the biopsy needle retained by the puncture instrument 10a in the rotation and angulation axes and for setting a stop position along the depth axis, respectively. Positional feedback is provided to the biopsy needle positioning motor controller by the three DC motors 12a, 14a, and 16a. The operator hand controller allows the clinician user to control the motorized biopsy needle positioning system. Controls are provided to permit the user to initiate movement of the biopsy needle into a position for insertion to the identified point of interest within the patient's breast, in accordance with the computed spatial coordinates of that point of interest The position of the biopsy needle may be monitored by the user with reference to a 32-character display on the operator hand controller. An enable switch is provided to prevent inadvertent motion of the biopsy needle.

The remote view and display box receives the spatial coordinates of rotation, angulation, and depth from the biopsy needle positioning motor controller and displays them for the benefit of the clinician user or others on a 40-character alphanumeric display. The remote view and display box may be conveniently mounted on a table that includes means for mounting and lighting x-ray reference films to be viewed during a breast biopsy procedure.

Figure 16:
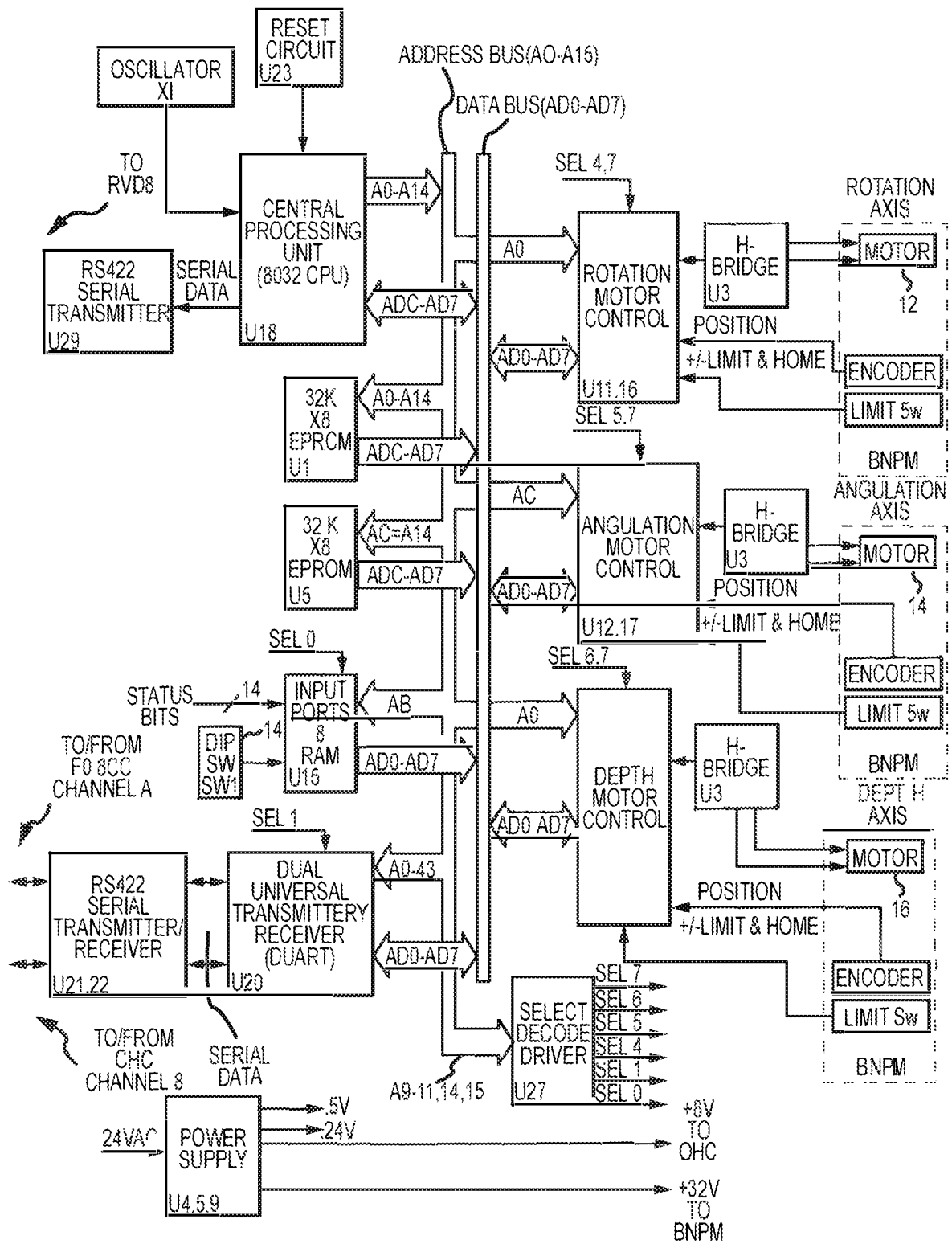

Operation of the biopsy needle positioning motor controller may be understood with reference to the detailed block diagram of FIG. 16. The biopsy needle positioning motor controller receives the spatial coordinates of the identified point of interest within the patient's breast from the film digitizer and coordinates calculator and computes the variables required to drive the three DC motors 12a, 14a, and 16a that form part of the biopsy needle positioning mechanism. Information regarding the position of the biopsy needle is continuously provided by the biopsy needle positioning motor controller to the LED displays in the operator hand controller. During manual operation, the biopsy needle positioning motor controller receives commands from the operator hand controller and drives the biopsy needle positioning mechanism in the direction specified for as long as the user simultaneously depresses one of the direction arrow keys and the enable switch located on the operator hand controller illustrated in FIG. 17.

A central processing unit (8032 CPU) within the biopsy needle positioning motor controller has a direct serial communications link with the remote view and display box through an RS422 serial transmitter U29. The 8032 CPU also has two bi-directional communications links through a dual synchronous universal transmitter/receiver DUART, which provides serial communications between the biopsy needle positioning motor controller and both the film digitizer and coordinates calculator (serial channel B) and the operator hand controller (serial channel A).

Under normal operating conditions, the 8032 CPU loads the three DC motor controller sections (rotation, angulation, and depth) with high level initial conditions data. This initial conditions data includes velocity constants, acceleration constants, PID filter information, and sample period. When the spatial coordinates of the identified point of interest within the patient's breast, as computed by the film digitizer and coordinates calculator, are placed on the data bus ADO-AD7 by DUART U11, the 8032 CPU reads these spatial coordinates and calculates the corresponding motor control values. The 8032 CPU then sends this data to the three motor control sections. The motor control sections calculate the actual motor drive voltages and provide the drive voltages to motors 12a, 14a, and 16a through separate H-bridge circuits. The motor control sections monitor the encoder feedback from the biopsy needle positioning mechanism to determine the position of the biopsy needle and to adjust the motor drive voltages as the biopsy needle reaches the identified point of interest. A typical motor voltage and velocity profile is trapezoidal in nature, ramping up to a start voltage, then holding constant, and finally ramping down to a stop voltage when the biopsy needle has reached the position required for insertion to the identified point of interest.

The 8032 CPU support circuits include operating and debug program data in erasable programmable read-only memories EPROMs U1 and U6. Fourteen status bits plus a six-bit DIP switch are monitored through an input port and a random access memory RAM U15. The status bits include +/−limit switches and a home switch associated with each coordinate axis. Two additional status bits serve to monitor the +5-volt (+5ENC) and +24-volt (+24VOK) power supplies. A reset circuit U23 provides a reset signal to reset the 8032 CPU when power is initially applied. The reset circuit also monitors program execution by counting a pulse associated with each cycle of the program and by executing a CPU reset command if the pulses stop, as may occur during a software lockup.

Figure 17:
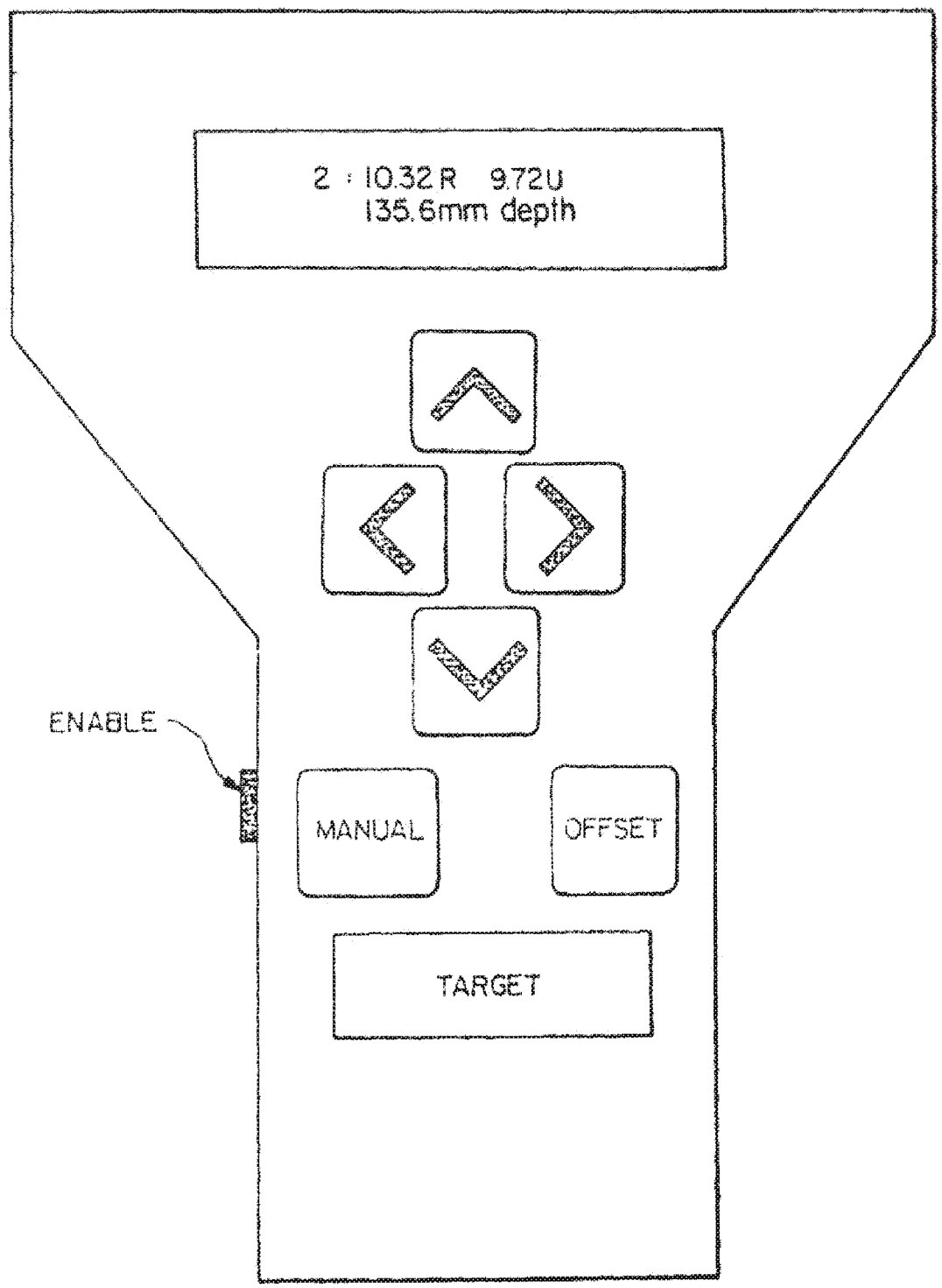
Figure 18:
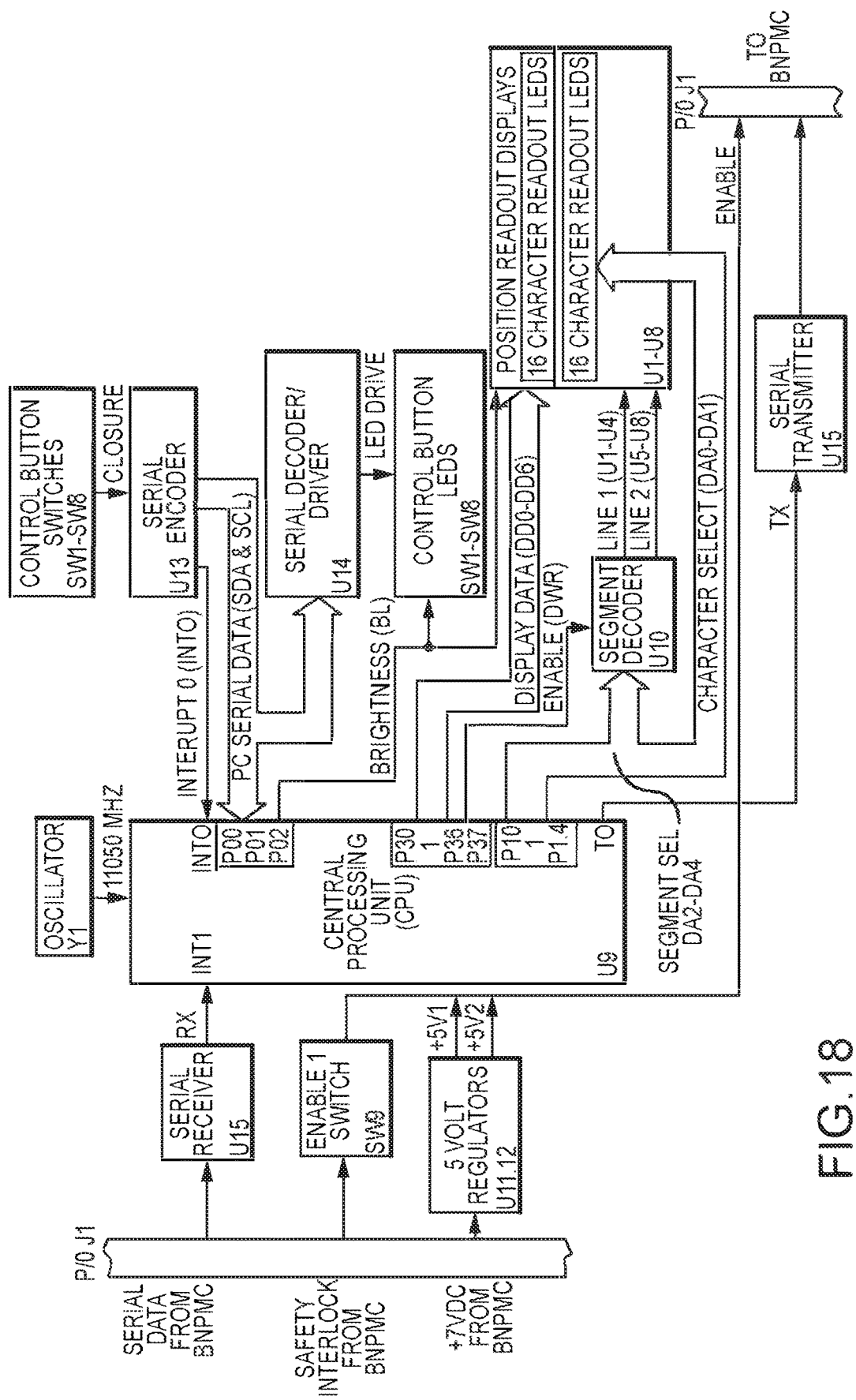

Referring now to FIGS. 17 and 18, it will be understood how the operator hand controller of FIG. 17 transmits data to and receives data and instructions from the biopsy needle positioning motor controller via an RS422 serial transmitter/receiver bus (serial channel A). While the operator hand controller is described herein as being a hand-held unit, it may also comprise a console or table-mounted unit. The principal functions of the operator hand controller are to 1) transmit switch closure data resulting from actuation of the direction arrow keys and the MANUAL, OFFSET, and TARGET keys to the biopsy needle positioning motor controller; 2) illuminate button LEDs in accordance with information received from the biopsy needle positioning motor controller; and 3) display the spatial coordinates of the identified point of interest within the patient's breast, as provided by the biopsy needle positioning motor controller. Additionally, the operator hand controller provides a safety interlock through the ENABLE switch SW9, which must be simultaneously depressed by the user with a selected one of the function keys in order to initiate any of the functions of the operator hand controller. The ENABLE switch is mounted on the side of the operator hand controller and, when depressed, energizes a relay in the biopsy needle positioning motor controller that enables movement of the biopsy needle positioning mechanism. When this switch opens, the relay removes power from the three DC motors 12a, 14a, and 16a of the biopsy needle positioning mechanism.

The clinician user initiates control of the biopsy needle positioning mechanism in either an automatic or manual mode by depressing control switches on the operator hand controller. Depressing one of the arrow keys or one of the MANUAL, OFFSET or TARGET keys has the effect of grounding a corresponding input of serial encoder U 13. This causes serial encoder U13 to apply an INTERRUPT 0 (INTOO) to the CPU U9 and place the serial data in 12C protocol on the serial lines SDA and. SCL to the CPU U9. The CPU U9 converts the switch information to RS422 protocol and sends it to the biopsy needle positioning motor controller via serial transmitter U15. Each of the keys on the operator hand controller contains a light emitting diode LED that is illuminated under the control of the biopsy needle positioning motor controller. The biopsy needle positioning motor controller selects a particular LED to be illuminated, sets the brightness of that LED, and determines how long that LED is to remain illuminated. This information is sent to the CPU U9 via serial receiver U15. The CPU U9 then places the information in 12C protocol on the serial lines SDA and SCL to be transmitted to serial decoder/driver U14. Serial decoder/driver U14 pulls a corresponding output to its low state, thereby illuminating the selected LED. The CPU U9 controls the brightness of the LEDs on the operator hand controller by setting the duty cycle of BRIGHTNESS (BL) pulses applied to the LEDS. A 50% duty cycle illuminates the LEDs at half brightness and a 100% duty cycle illuminates the LEDs at full brightness.

The position readout displays U1-U8 in the operator hand controller provide two rows of displayed information comprising 16 ASCII characters in each row. Each row comprises four display devices, and each display device contains four 5.times.7 dot matrix character displays. Referring to FIG. 4, the top line of the position readout display indicates target number 2 (2:), a rotation axis angle of 10.32 degrees right (10.32 R), and an angulation axis angle of 9.72 degrees up (9.72 U). The bottom line of the position readout display indicates a depth stop setting of 135.6 millimeters (135.6 mm depth). As previously described in connection with the LEDs that illuminate each of the keys of the operator hand controller, the biopsy needle positioning motor controller similarly controls the position readout displays through serial communications with the operator hand controller CPU U9. The CPU U9 provides segment selection control and character display using two data buses DDO-DD7 and DAO-DA4. To display a selected ASCII character, the CPU U9 puts data describing the character on the DDO-DD7 (P3.0-P3.6 outputs of the CPU U9) bus. The CPU U9 transmits a low signal FNABLE (DWR) to segment decoder U10, which decodes bits DA2-DA4 and applies a low enable signal to the appropriate ones of display device U1-U8. The enabled display device then decodes the character select bit DAO and DA1 to select the character position which displays the ASCII character defined by data bus DDO-DD6. As with the LEDs, the biopsy needle positioning motor controller defines the brightness of the position readout display. The biopsy needle positioning motor controller communicates the brightness level to the CPU U9, which then switches the BRIGHTNESS (BL) signal on and off, producing the designated duty cycle.

In addition, an additional line 106 can be added for introducing anesthetic and/or contrast agents, for example, along with a flushing agent or lavage. The introduction of the anesthetic and/or contrast agents can be automated and synchronized to the imaging sequence.

Many variations can be introduced on the above-discussed illustrative embodiments and examples without departing from the spirit of the disclosure or from the scope of the appended claims. For example, elements and/or features of different examples and illustrative embodiments may be combined with each other and/or substituted for each other within the scope of this disclosure and appended claims.

What is claimed is:

1. A method for performing a biopsy of a breast of a patient based on contrast-enhanced tomosynthesis reconstructed images, the method comprising:
   positioning a needle in the breast, based in part on three-dimensional coordinates of an area of interest;
   performing a pre-fire tomosynthesis scan of the breast, while the breast contains a contrast agent, the pre-fire tomosynthesis scan comprising:
      moving an imaging x-ray source through a plurality of imaging positions along a source trajectory;
      emitting a plurality of pre-fire x-ray beams from the imaging x-ray source at the plurality of imaging positions, wherein at least two of the plurality of pre-fire x-ray beams correspond to at least a first x-ray dose and a second x-ray dose different than the first x-ray dose;
      obtaining a plurality of pre-fire images corresponding to each of the plurality of imaging positions, the plurality of pre-fire images comprising a first set of images and a second set of images; and
      based on the first set of images and the second set of images, deriving pre-fire tomosynthesis reconstructed images representing respective slices of the breast; and
   firing the needle.

2. The method of claim 1, further comprising displaying a subset of the pre-fire tomosynthesis reconstructed images.

3. The method of claim 2, further comprising eliminating from subsequent display at least one of the subset of the pre-fire tomosynthesis reconstructed images.

4. The method of claim 3, wherein the elimination of the at least one of the subset of the pre-fire tomosynthesis reconstructed images is based on image artifacts on the breast.

5. The method of claim 1, the method further comprising:
   after firing the needle, performing post-fire imaging of the breast, while the breast contains the contrast agent, wherein performing the post-fire imaging comprises:
      obtaining, at a first imaging position, a first image; and
      obtaining, at a second imaging position, a second image; and
   based on the first image and the second image, deriving contrast-enhanced post-fire tomosynthesis images.

6. The method of claim 5, wherein the first imaging position and the second imaging position are disposed asymmetrically to the needle.

7. The method of claim 1, the method further comprising:
   after firing the needle, performing post-fire imaging of the breast, while the breast contains the contrast agent, wherein performing the post-fire imaging comprises:
      obtaining, at a first imaging position, a first image; and
      obtaining, at a second imaging position, a second image; and
   based on the first image and the second image, deriving a contrast-enhanced post-fire stereotactic image.

8. The method of claim 1, placing a mark corresponding to the area of interest on one or more of the pre-fire tomosynthesis reconstructed images.

9. The method of claim 1, wherein positioning the needle in the breast is performed by one of a motorized mechanism, manually, or operating a hand-operated device.

10. The method of claim 1, wherein the source trajectory includes a gap region, the first x-ray dose occurring at positions of the imaging x-ray source within the gap region.

11. A system for performing a biopsy of a breast of a patient based on contrast-enhanced tomosynthesis reconstructed images, the system comprising:
    an imaging x-ray source;
    an x-ray detector;
    a biopsy needle assembly with a needle;
    a processor operatively coupled to the imaging x-ray source, the x-ray detector, and the biopsy needle assembly; and
    memory storing instructions that, when executed by the processor cause the system to perform a set of operations comprising:
        positioning the needle in the breast, based in part on three-dimensional coordinates of an area of interest;
        performing a pre-fire tomosynthesis scan of the breast, while the breast contains a contrast agent, the pre-fire tomosynthesis scan comprising:
            moving the imaging x-ray source through a plurality of imaging positions along a source trajectory;
            emitting a plurality of pre-fire x-ray beams from the imaging x-ray source at the plurality of imaging positions, wherein at least two of the plurality of pre-fire x-ray beams correspond to at least a first x-ray dose and a second x-ray dose different than the first x-ray dose;
            obtaining a plurality of pre-fire images corresponding to each of the plurality of imaging positions, the plurality of pre-fire images comprising a first set of images and a second set of images; and
            based on the first set of images and the second set of images, deriving pre-fire tomosynthesis reconstructed images representing respective slices of the breast; and
        firing the needle.

12. The system of claim 11, further comprising a display configured to display a subset of the pre-fire tomosynthesis reconstructed images.

13. The system of claim 12, wherein the set of operations further comprises eliminating from subsequent display at least one of the subset of the pre-fire tomosynthesis reconstructed images.

14. The system of claim 11, wherein the set of operations further comprises:
    after firing the needle, performing post-fire imaging of the breast, while the breast contains the contrast agent, wherein performing the post-fire imaging comprises:
        obtaining, at a first imaging position, a first image; and
        obtaining, at a second imaging position, a second image; and
    based on the first image and the second image, deriving contrast-enhanced post-fire tomosynthesis images.

15. The system of claim 11, wherein the set of operations further comprises:
    after firing the needle, performing post-fire imaging of the breast, while the breast contains the contrast agent, wherein performing the post-fire imaging comprises:
        obtaining, at a first imaging position, a first image; and
        obtaining, at a second imaging position, a second image; and
    based on the first image and the second image, deriving a contrast-enhanced post-fire stereotactic image.

16. The system of claim 11, wherein the needle includes two metallic tips and two needle stems, one of the two needle stems having a notch, and wherein the two needle stems are formed from an x-ray transparent material.

17. The system of claim 16, wherein the two needle stems include one or more removable x-ray opaque ribs.

18. The system of claim 16, wherein the two needle stems include a removable x-ray opaque strength layer.

19. The system of claim 11, wherein the set of operations further comprises processing the plurality of pre-fire images to reduce image artifacts contained therein.

20. The system of claim 11, wherein the set of operations further comprises determining the plurality of imaging positions by avoiding or reducing use of imaging positions that result in image artifacts from the needle.

* * * * *